(12) United States Patent
Caluser et al.

(10) Patent No.: US 12,059,295 B2
(45) Date of Patent: *Aug. 13, 2024

(54) THREE DIMENSIONAL MAPPING DISPLAY SYSTEM FOR DIAGNOSTIC ULTRASOUND

(71) Applicant: Metritrack, Inc., Hillside, IL (US)

(72) Inventors: Calin Caluser, Glen Ellyn, IL (US); Fang Lin, Elmhurst, IL (US); Silviu S. Andrei, Las Vegas, NV (US)

(73) Assignee: Metritrack, Inc., Hillside, IL (US)

( * ) Notice: Subject to any disclaimer, the term of this patent is extended or adjusted under 35 U.S.C. 154(b) by 311 days.

This patent is subject to a terminal disclaimer.

(21) Appl. No.: 17/468,061

(22) Filed: Sep. 7, 2021

(65) Prior Publication Data

US 2022/0047244 A1 Feb. 17, 2022

Related U.S. Application Data

(63) Continuation of application No. 13/719,200, filed on Dec. 18, 2012, now Pat. No. 11,109,835.
(Continued)

(51) Int. Cl.
*A61B 8/00* (2006.01)
*A61B 8/08* (2006.01)
(Continued)

(52) U.S. Cl.
CPC .......... *A61B 8/4254* (2013.01); *A61B 8/0825* (2013.01); *A61B 8/10* (2013.01);
(Continued)

(58) Field of Classification Search
None
See application file for complete search history.

(56) References Cited

U.S. PATENT DOCUMENTS

| 5,438,996 A | 8/1995 | Kemper et al. |
| 5,911,126 A | 6/1999 | Massen |

(Continued)

FOREIGN PATENT DOCUMENTS

| CN | 100548223 C | 10/2009 |
| EP | 1623674 A1 | 2/2006 |

(Continued)

OTHER PUBLICATIONS

Pagoulatos et al., Interactive 3-D Registration of Ultrasound and Magnetic Resonance Images Based on a Magnetic Position Sensor,: IEEE Transactions on Information Technology in Biomedicine, vol. 3, No. 4, Dec. 1999, pp. 278-288.

(Continued)

*Primary Examiner* — Shahdeep Mohammed
(74) *Attorney, Agent, or Firm* — Vedder Price P.C.

(57) ABSTRACT

An automated three dimensional mapping and display system for a diagnostic ultrasound system is presented. According to the invention, ultrasound probe position registration is automated, the position of each pixel in the ultrasound image in reference to selected anatomical references is calculated, and specified information is stored on command. The system, during real time ultrasound scanning, enables the ultrasound probe position and orientation to be continuously displayed over a body or body part diagram, thereby facilitating scanning and images interpretation of stored information. The system can then record single or multiple ultrasound free hand two-dimensional (also "2D") frames in a video sequence (clip) or cine loop wherein multiple 2D frames of one or more video sequences corresponding to a scanned volume can be reconstructed in three-dimensional (also "3D") volume images corresponding to the scanned region, using known 3D reconstruction algorithms. In later examinations, the exact location and position of the trans- (Continued)

ducer can be recreated along three dimensional or two dimensional axis points enabling known targets to be viewed from an exact, known position.

12 Claims, 41 Drawing Sheets

Related U.S. Application Data

(60) Provisional application No. 61/577,029, filed on Dec. 18, 2011.

(51) Int. Cl.
*A61B 8/10* (2006.01)
*A61B 8/13* (2006.01)

(52) U.S. Cl.
CPC .............. *A61B 8/13* (2013.01); *A61B 8/4263* (2013.01); *A61B 8/463* (2013.01); *A61B 8/466* (2013.01); *A61B 8/483* (2013.01); *A61B 8/5207* (2013.01); *A61B 8/5246* (2013.01); *A61B 8/5292* (2013.01); *A61B 8/54* (2013.01); *A61B 8/56* (2013.01); *A61B 8/58* (2013.01); *A61B 8/4227* (2013.01)

(56) References Cited

U.S. PATENT DOCUMENTS

| | | | |
|---|---|---|---|
| 6,171,244 B1 | 1/2001 | Finger et al. | |
| 6,203,497 B1 | 3/2001 | Dekel et al. | |
| 6,261,247 B1 | 7/2001 | Ishikawa et al. | |
| 6,390,982 B1 | 5/2002 | Bova et al. | |
| 6,500,118 B1 | 12/2002 | Hashimoto | |
| 6,669,653 B2 | 12/2003 | Paltieli | |
| 6,675,038 B2 | 1/2004 | Cupples et al. | |
| 7,176,916 B2 | 2/2007 | Riaz | |
| 7,220,955 B2 | 5/2007 | Brunfeld et al. | |
| 7,229,411 B2 | 6/2007 | Slayton et al. | |
| 7,238,158 B2 | 7/2007 | Abend | |
| 7,244,230 B2 | 7/2007 | Duggirala et al. | |
| 7,251,352 B2 | 7/2007 | Sauer et al. | |
| 7,255,695 B2 | 8/2007 | Falwell et al. | |
| 7,259,897 B2 | 8/2007 | Garlick et al. | |
| 7,260,426 B2 | 8/2007 | Schweikard et al. | |
| 7,639,895 B2 | 12/2009 | Sakas et al. | |
| 9,471,981 B2 | 10/2016 | Arai et al. | |
| 2002/0049375 A1 | 4/2002 | Strommer et al. | |
| 2004/0106869 A1 | 6/2004 | Tepper | |
| 2005/0020917 A1 | 1/2005 | Scherch | |
| 2005/0129299 A1 | 6/2005 | Kreang-Arekul et al. | |
| 2005/0251028 A1 | 11/2005 | Boese et al. | |
| 2006/0247918 A1 | 11/2006 | Schmidt et al. | |
| 2007/0023671 A1 | 2/2007 | Britten | |
| 2007/0055150 A1 | 3/2007 | Donaldson et al. | |
| 2007/0083117 A1 | 4/2007 | Sakas et al. | |
| 2007/0167801 A1 | 7/2007 | Webler et al. | |
| 2007/0167805 A1 | 7/2007 | Clement | |
| 2007/0239004 A1 | 10/2007 | Kakee et al. | |
| 2008/0085042 A1 | 4/2008 | Trofimov et al. | |
| 2008/0095421 A1 | 4/2008 | Sun et al. | |
| 2008/0200808 A1 | 8/2008 | Leidel et al. | |
| 2008/0221446 A1 | 9/2008 | Washburn et al. | |
| 2008/0249401 A1* | 10/2008 | Watanabe | A61B 8/13 600/437 |
| 2008/0262338 A1 | 10/2008 | Paitel et al. | |
| 2009/0124906 A1 | 5/2009 | Caluser | |
| 2011/0028844 A1 | 2/2011 | Hyun et al. | |
| 2011/0182493 A1 | 7/2011 | Huber et al. | |

FOREIGN PATENT DOCUMENTS

| | | |
|---|---|---|
| WO | 1998039669 A1 | 9/1998 |
| WO | 2006008300 A1 | 1/2006 |

OTHER PUBLICATIONS

Office Action and English Translation of related Chinese Application No. 201380073261.X, dated Oct. 28, 2016.

* cited by examiner

THREE DIMENSIONAL MAPPING DISPLAY SYSTEM FOR DIAGNOSTIC ULTRASOUND

CROSS-REFERENCE TO RELATED APPLICATIONS

This application is a continuation of and claims the benefit of priority from U.S. application Ser. No. 13/719,200, filed Dec. 18, 2012, which claims the benefit of an priority to U.S. Provisional Application No. 61/577,029, filed Dec. 18, 2011, the contents of each of which are hereby fully incorporated herein by reference.

TECHNICAL FIELD

The present invention relates to diagnostic ultrasound technology and, more particularly, to a three dimensional mapping display ("TDMD") diagnostic ultrasound system in which ultrasound probe position registration is automated, the position of each pixel in the ultrasound image in reference to preselected anatomical references is calculated, and specified information is stored on command. Moreover, the system, during real time ultrasound scanning enables the ultrasound probe position and orientation to be continuously displayed over a body or body part diagram, thereby facilitating the storage of information. The TDMD can then record multiple ultrasound free hand two-dimensional (also, "2D") frames in a video sequence (clip) or cine loop wherein multiple 2D frames of one or more video sequences corresponding to a scanned volume can be reconstructed in three-dimensional (also, "3D") volume images corresponding to the scanned region, using known 3D reconstruction algorithms.

BACKGROUND OF THE INVENTION

Ultrasound is an important imaging modality for medical diagnostic purposes and as a guidance tool for diagnostic or therapeutic procedures, like soft tissue needle biopsy, tumor ablation, etc. Ultrasound can be used over the entire human body and has certain advantages over other modalities, including, among others: the ability to locate and characterize medical problems; lower cost compared to modalities such as MM and CT; real time operation; and, the lack of ionizing radiation with the known associated health risks.

Ultrasound imaging systems transmit sound waves of very high frequency (e.g., 1 MHz to 20 MHz) into the patient's body and the echoes scattered from structures in the patient's body are processed to create and display images and information related to these structures.

Ultrasound imaging can be applied to various regions or organs in the body. For example, a breast ultrasound procedure involves the placement of an ultrasound transducer over a region of interest of the breast, with the radiologist or other medical professional (the "user") viewing a real-time ultrasound image output on a display. The ultrasound machine monitor usually displays relevant text and/or graphical information next to the ultrasound image for simultaneous viewing by the user. The user can freeze a displayed image with medical findings of interest, and the corresponding image can be printed on a printer or stored in digital format.

2D free hand ultrasound imaging, the most common technique used today, represents a slice through the region of interest. 3D ultrasound scanning is available; however, it is usually used in conjunction with 2D scanning techniques. Currently, most diagnostic studies are performed using 2D scanning technique.

The vast majority of ultrasound guided biopsies and other invasive ultrasound guided invasive procedures done by free hand and other more automated modes use the ultrasound machine 2D display mode. Therefore, it is desirable to have a fast and accurate way to find the target during such invasive procedures.

It is important to accurately store positional annotations for later evaluation, since this is essential for final interpretation, diagnosis, and treatment. As digital storage and communication of medical information replace hard copy based storage and communication technologies, the accurate and consistent annotation of ultrasound and other medical images is critical. Correlation of ultrasound images with images of the same body region obtained with other modalities (MM, CT, mammograms, PET, etc.) becomes increasingly important for medical diagnostic and therapeutic purposes. As a result, precise positional registration of the targets is important.

This importance is illustrated by noting that finding a small tumor can save a patient's life. The smaller the tumor is before treatment, the higher the probability of long term patient survival or cure; however, a small tumor is difficult to find in a patient's body and differentiate from other structures or artifacts in the same region. Many times a suspicious small finding can coexist in the same region with multiple benign findings (cysts, solid benign nodules, etc.) with similar appearance, which may create confusion during a follow up exam and may lead to missing the suspicious lesion. As imaging diagnostic devices provide ever greater detail and sub-millimeter resolution, accurate position registration and mapping of lesions is becoming increasingly important in order to take advantage of the increased capabilities.

Ultrasound procedures are highly dependent on the device user's experience and training. Position recording of certain findings is important, especially for the small targets and/or multiple targets. Most frequently, an ultrasound user will hold the ultrasound transducer in one hand and use the other hand to operate the ultrasound machine controls. It is desirable to obtain the instant recording of target coordinates seen in the ultrasound image in relation to the anatomical reference (for example, a nipple) and the simultaneous recording of the transducer position. Currently, the automated recording of the transducer position in real time scanning is limited due to the motion of the pre-selected anatomical reference secondary to body and transducer induced motion. Therefore, it is desirable to continuously update the position of the anatomical references, or landmarks, and apply the correction to the obtained measurements.

The American College of Radiology (ACR) recommends that all ultrasound images be properly labeled. For example, for breast ultrasound images, the findings position, in hourly format, distance from Nipple C and ultrasound probe position and orientation should be displayed with the ultrasound images. Currently, ultrasound findings are manually labeled by an operator, which is time consuming and prone to errors. Manual labeling involves the typing of an approximate position in the organ or part of the body, since an accurate position registration is time consuming and, importantly, difficult for the user.

Although multiple ultrasound guidance systems and devices already exist, they do not offer a practical and accurate solution to mapping patient findings in 2D or 3D images in relation to set anatomical reference(s) which is operator independent during a routine examination, with real time correction for the patient's motion. It would be beneficial, therefore, to obtain the accurate position of selected targets in the ultrasound images in relation to set anatomical reference point(s) with the corresponding ultrasound probe position and orientation by selecting the target in the ultrasound image at the time of examination or at a later date in the stored images with attached positional information. The present invention provides such an advance to the art.

OBJECTS AND ADVANTAGES OF THE PRESENT INVENTION

It is an object of the present invention to significantly reduce the time of the examination by eliminating the time consuming manual labeling of images and speeding up the target finding at subsequent examinations.

It is a further object of the present invention to obtain the accurate position of selected targets in ultrasound images in relation to set anatomical reference(s) with the corresponding ultrasound probe position and orientation by selecting the target in the ultrasound image at the time of examination or at a later time or at a later date in the stored images with attached positional information in both 2D or 3D imaging techniques.

It is a further object of the present invention to enhance correlation capability with other diagnostic imaging modalities like CT scans, MM, mammograms etc.

It is yet a further object of the present invention to eliminate or minimize errors due to inaccurate position labeling and excessive artifacts, therefore reducing the risk of costly lawsuits due to missed diagnosis and decrease the number of callbacks for the patients for repeat examination.

It is yet a further object of the present invention to provide a sensor attaching device to enable accurate sensor placement and adherence and to, further, reduce the chance of operator error.

One advantage, among the many that will be appreciated by those skilled in the arts, is that the present invention provides an easy, uniform, method of communicating the target position among healthcare providers by guiding the ultrasound to a previously recorded target through following the real time display of the ultrasound transducer position in relation to the target coordinates from a previous examination.

SUMMARY OF THE INVENTION

The present invention provides an apparatus and method of use for automated ultrasound probe position registration, calculating the position of each pixel in the ultrasound image in dynamic reference to the selected anatomical references (AR), and storing selected information on demand. The present invention further enables, during real time ultrasound scanning, continuous ultrasound probe position and orientation display, which display be permanently stored in the system's memory at the users command.

The Present invention comprises a hardware/software application and real time commercial 3D position registration system interfaced with an ultrasound machine.

After initial calibration and selection of one or more anatomical references (nipple, umbilicus, skull, etc.), positional information associated with each individually recorded image frame or each image in a cine loop is stored with the corresponding image. Using a pointing device with the system display, spatial numerical coordinates of the selected pixel or region, including the distance from the anatomical reference, depth, angle to the body axis and a graphical representation, are displayed next to the ultrasound image. Also displayed are the real time position of the ultrasound probe and target position in a body diagram or other representation shown with the real time ultrasound image, to help the ultrasound operator during scanning. The data from the positional sensors is used to perform the dynamic coregistration of the real time ultrasound image, first image set, with the breast or other body part representation, the second image set, in the same spatial coordinate frame. The real time ultrasound image can be coregistered with any number of sets of images previously recorded.

Each saved ultrasound image or set of images in a cine loop will have attached positional information corresponding to each pixel in the ultrasound frame and the diagram with the body part with the ultrasound probe position and orientation in reference to the anatomical reference(s) and position of a target pixel(s), if any pixels are selected. In one embodiment the anatomical reference sensor (48) can be applied at the nipple of the breast (C) when the corresponding breast is examined with the ultrasound machine. Other body parts or regions can be recorded with corresponding anatomical reference(s) for example: liver with umbilicus, neck with thyroid cartilage etc. Target pixel selection can be made at the time of the image capture, before saving the image, or at a later time at the review station.

During future examinations, the user is guided to the target by entering the target coordinates obtained at the previous examination, display the target in the body diagram and adjust the probe position in the real time body diagram to overlap the target.

For the accurate automated recording of body targets and probe position related to certain anatomical references, a user continuously obtains positional information from selected anatomical references sensors and the probe positional coordinates are instantly updated.

This is achieved by continuously monitoring the preset anatomical references position, which in the preferred embodiment can be achieved with a magnetic sensor placed next to the anatomical reference on the skin. In an alternate embodiment the anatomical reference tracking can be obtained with an overhead tracking system using digital infrared or optical cameras with or without skin markers. In this embodiment, one camera can be used, or two or more cameras can also be used to achieve a three dimensional stereoscopic effect.

The TDMD can also be used to record multiple ultrasound free hand 2D frames in a video sequence (clip) or cine loop, with each frame saved with the positional coordinates as described above. When using the positional information in the multiple 2D frames of one or more video sequences corresponding to a scanned volume, the 2D images can be used to reconstruct 3D volume containing images corresponding to the scanned region, using known 3D reconstruction algorithms. The 3D volume reconstruction can be obtained from the original captured 2D ultrasound images or the segmented or otherwise processed 2D images in a video sequence. This embodiment is well suited for ultrasound breast cancer screening or diagnostic breast ultrasound exams and can also be applied to other regions in the body like, but not restricted to the eye, liver, abdomen, neck, kidneys, etc.

A sensor attaching device may also be employed to assist in the positioning and adherence of the magnetic or other type of positional sensors and to reduce operator error in the placement of the sensors and interference from connecting wire feedback.

There has been outlined, rather broadly, the more important features of the invention in order that the detailed description thereof that follows may be better understood, and in order that the present contribution to the art may be better appreciated. There are, of course, additional features of the invention that will be described hereinafter and that will form the subject matter of the invention.

DETAILED DESCRIPTION OF THE PREFERRED EMBODIMENT

Before explaining the preferred embodiment of the present invention in detail, it is to be understood that the present invention is not limited in its application to the details of arrangements of the components set forth in the following description. As will be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Unless defined otherwise, all technical and scientific terms used herein have the same meaning as commonly understood by one of ordinary skill in the art to which this invention belongs. Moreover, the singular forms "a", "an", and "the" include plural referents unless the context clearly dictates otherwise. Further, an ultrasound frame as herein described is same with 2D ultrasound image.

It should also be understood that the inventive device may include any of the features and respective hardware components described, or combinations thereof, however some features and components may make more practical sense for one particular use, depending on the particular design considerations and intended use.

Figure 1:
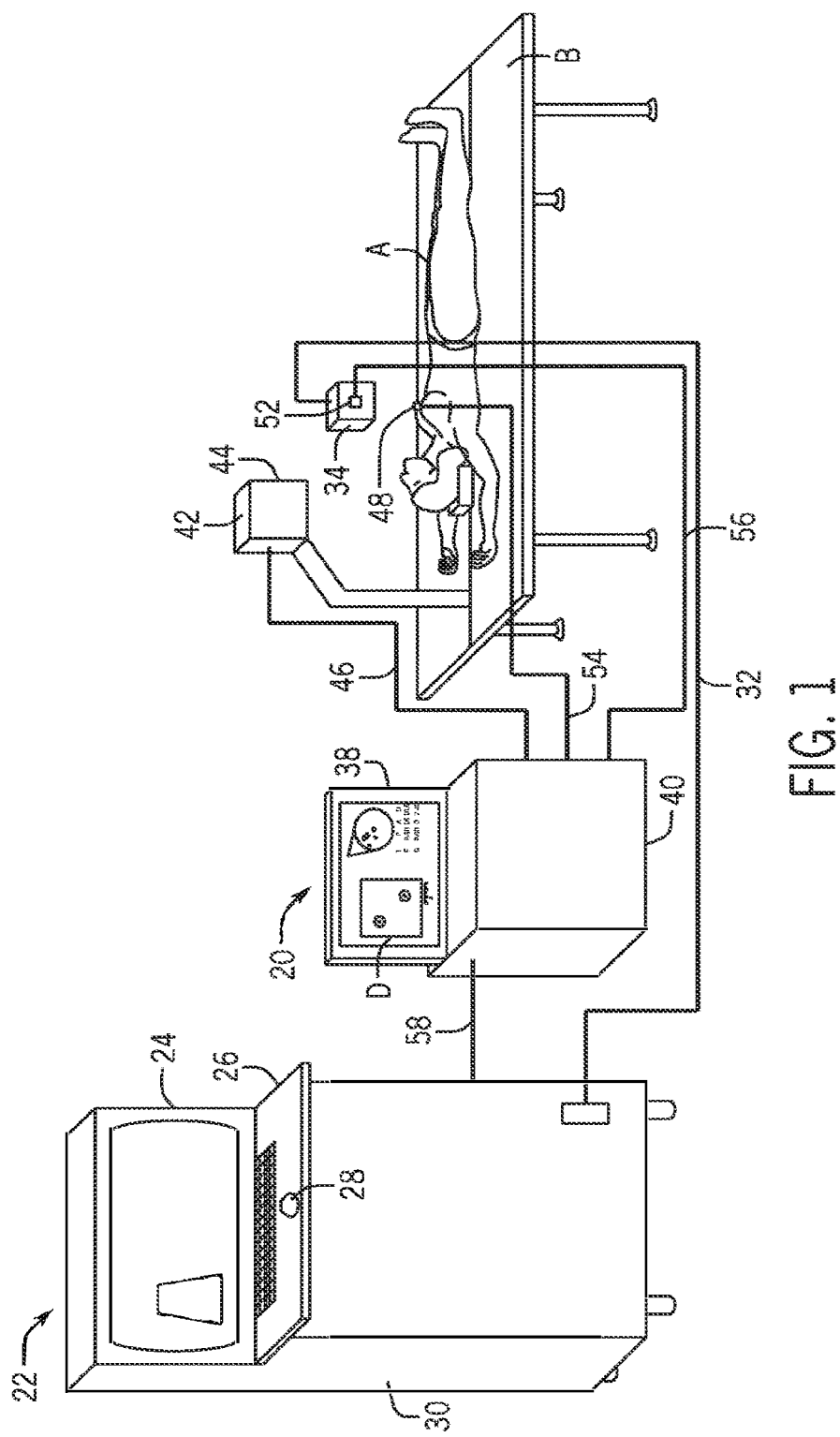
FIG. 1 depicts an overview illustration of the inventive apparatus placed in an ultrasound system.

Turning to FIG. 1, an over view of the physical aspects of an ultrasound device employing the inventive apparatus 20 is seen. Ultrasound machine 22 is a standard device including display 24, interface with keyboard 26 and pointer 28, chassis containing operating hardware (not seen) 30, probe connecting cord 32, and probe 34.

Figure 8:
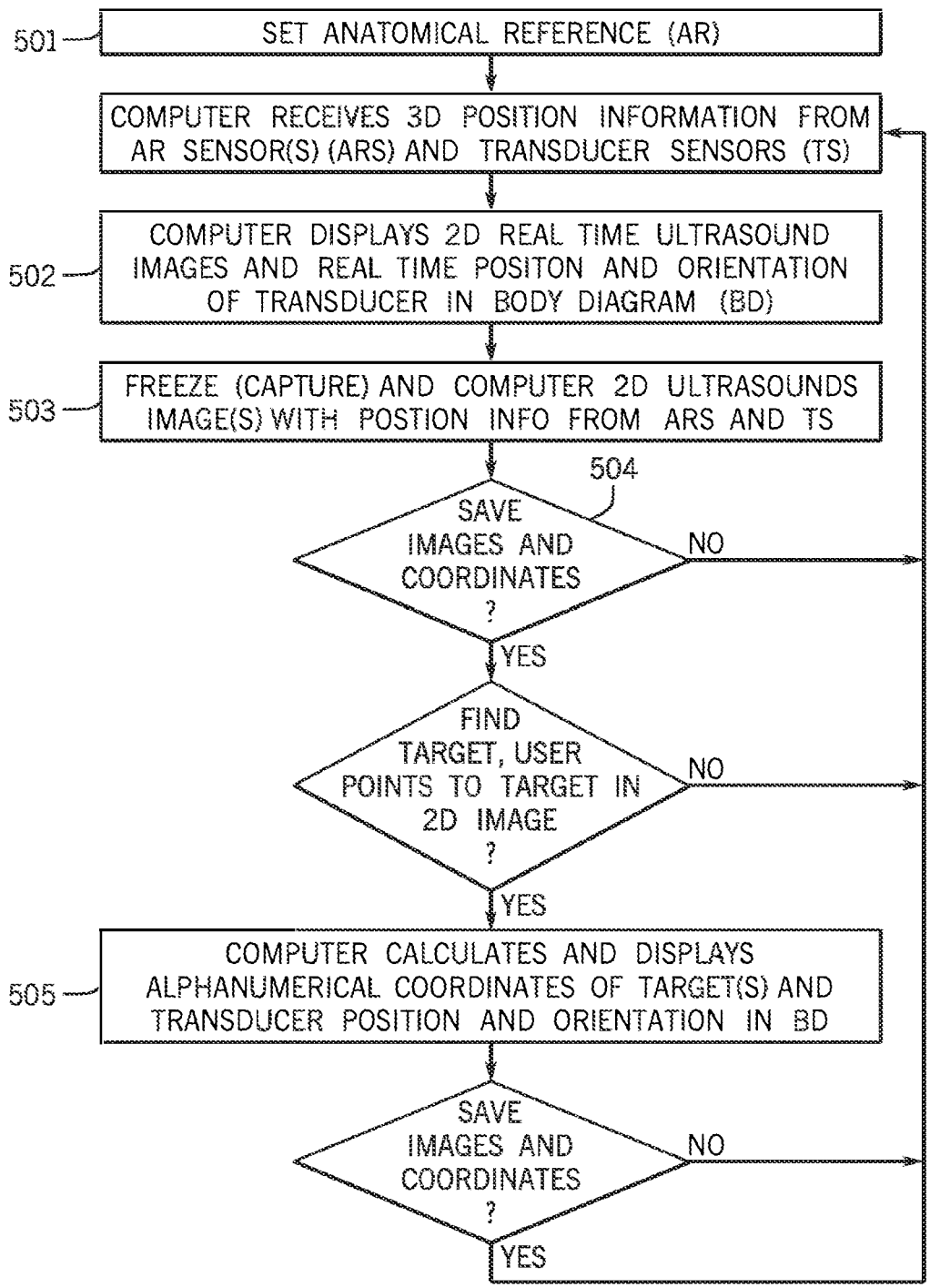
FIG. 8 illustrates the steps needed to measure and record the positional information associated with the diagnostic ultrasound images with a position sensor used for anatomical reference tracking.
Figure 9:
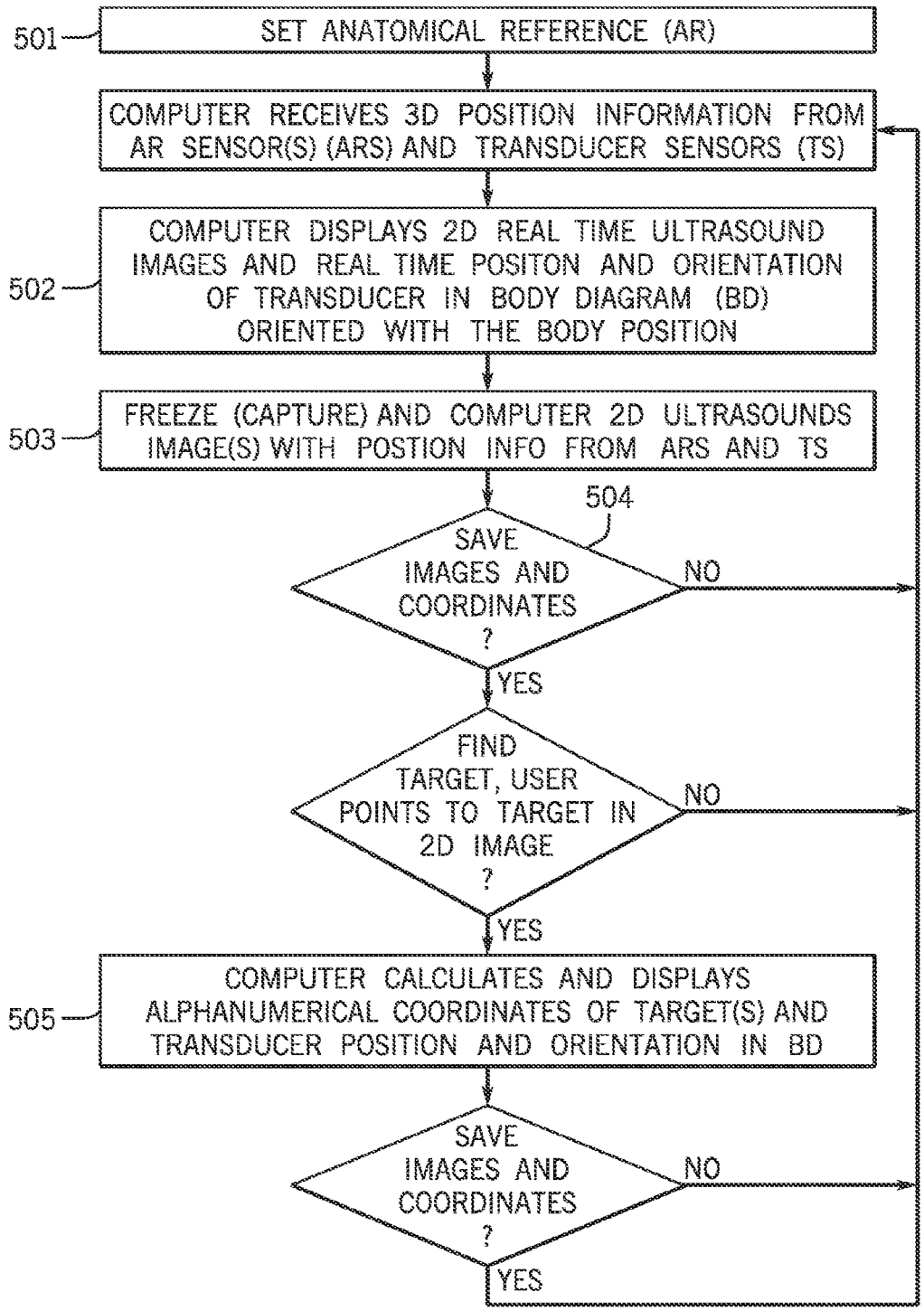
FIG. 9 illustrates the steps needed to measure and record the positional information associated with the diagnostic ultrasound images with a position sensor used for anatomical reference tracking and another position sensor for body position and orientation tracking.

Inventive apparatus (also referred to as three dimensional mapping display, or TDMD) 20 is depicted and comprises TDMD display 38, TDMD Chassis 40 containing hardware (also referred to as a "processor") and software (not seen; described in detail below), 3D magnetic tracking member 42 with the transmitter 44 connected to TDMD 20 by 3D magnetic tracking member cord 46, first magnetic sensor 48 connected to TDMD 20 by first magnetic sensor cord 54 and second magnetic sensor 52 connected to TDMD 20 by second magnetic sensor cord 56. A $3^{rd}$ position sternum sensor, 49 can be attached to track the patient's body position in reference to the exam table, FIG. 6. The sensors may also be of a wireless variety, thus sensor cords 56, 58 would not be required. Also a combination of wired and wireless position sensors can be used to provide the position tracking module with positional information from the tracked anatomical references and the ultrasound probe or probes. The positional sensors are used to dynamically track the ultrasound probe and patient's body landmarks that include selected anatomical references and other body locations and provide the data that can be used to coregister the ultrasound real time images with the body diagram or other secondary sets of images, to provide realistic position and orientation information about the ultrasound probe, images and the examined body region (FIG. 8, 502). As those skilled in the arts will understand, the principles of the present invention enable the use of a single display monitor or multiple display monitors for procedures. (For completeness in explaining FIGS. 1 and 6, patient A is situated on examining table B.)

Figure 2:
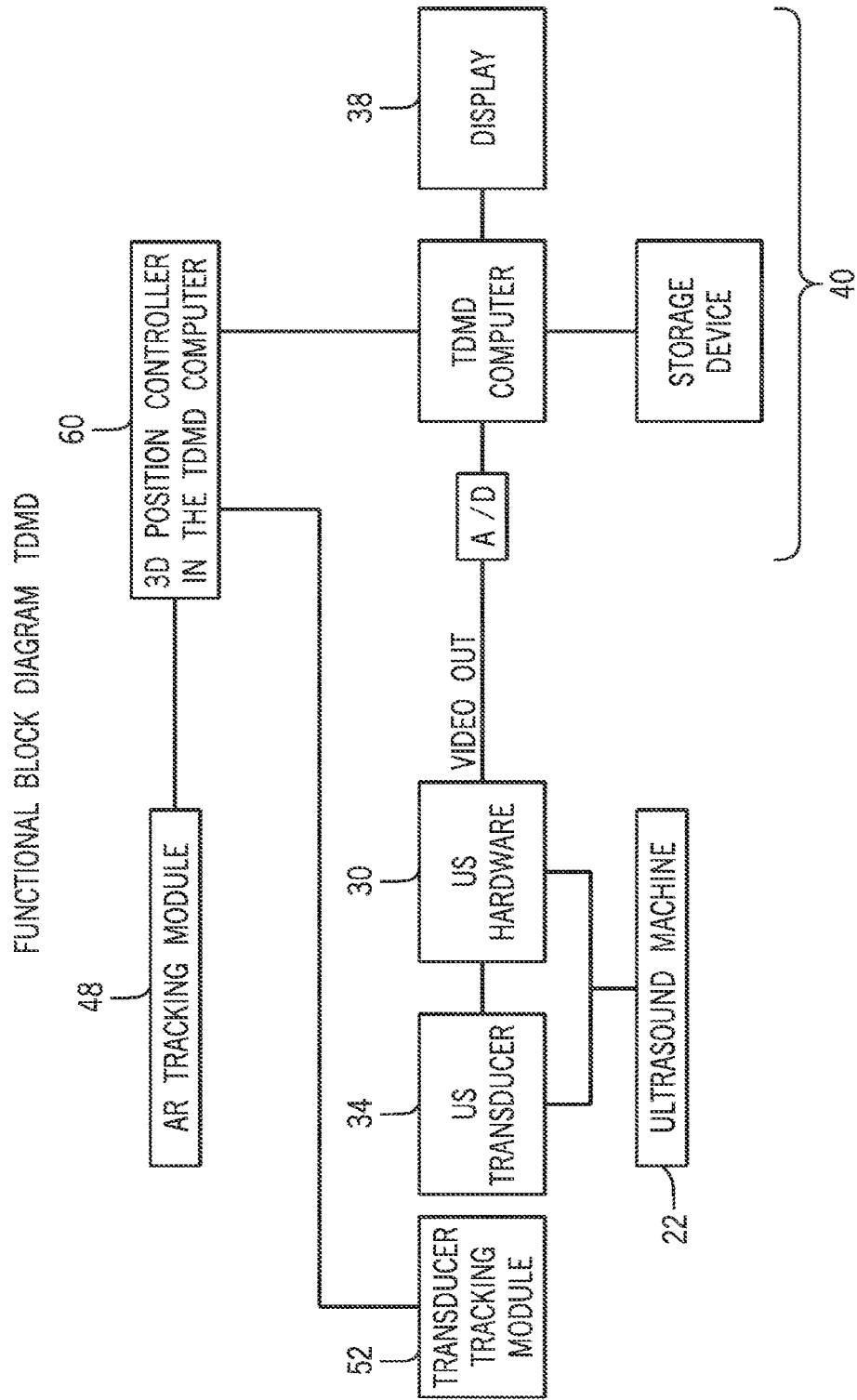
FIG. 2 illustrates the functional block diagram for the inventive device preferred embodiment with a magnetic sensor used for anatomical reference tracking and another magnetic sensor used for ultrasound probe tracking.

Turning to FIG. 2, a block diagram illustrating the various general working aspects of inventive device 20 is shown. First magnetic sensor (tracking module) 48 and second magnetic sensor (tracking module) 52 provide the positional information to the TDMD 20 3D position board/module 60. Video output 24 from ultrasound device 22 is digitized by the dedicated TDMD module/board 40. It should be noted that the analog to digital image conversion may not be needed if the ultrasound machine can be interfaced and it can directly provide the digital images to the TDMD 22.

TDMD can continuously track one or several anatomical reference markers or positional body markers, which can increase the overall accuracy of the system. If multiple positional body markers are used, not all of them need to be continuously tracked.

Figure 3:
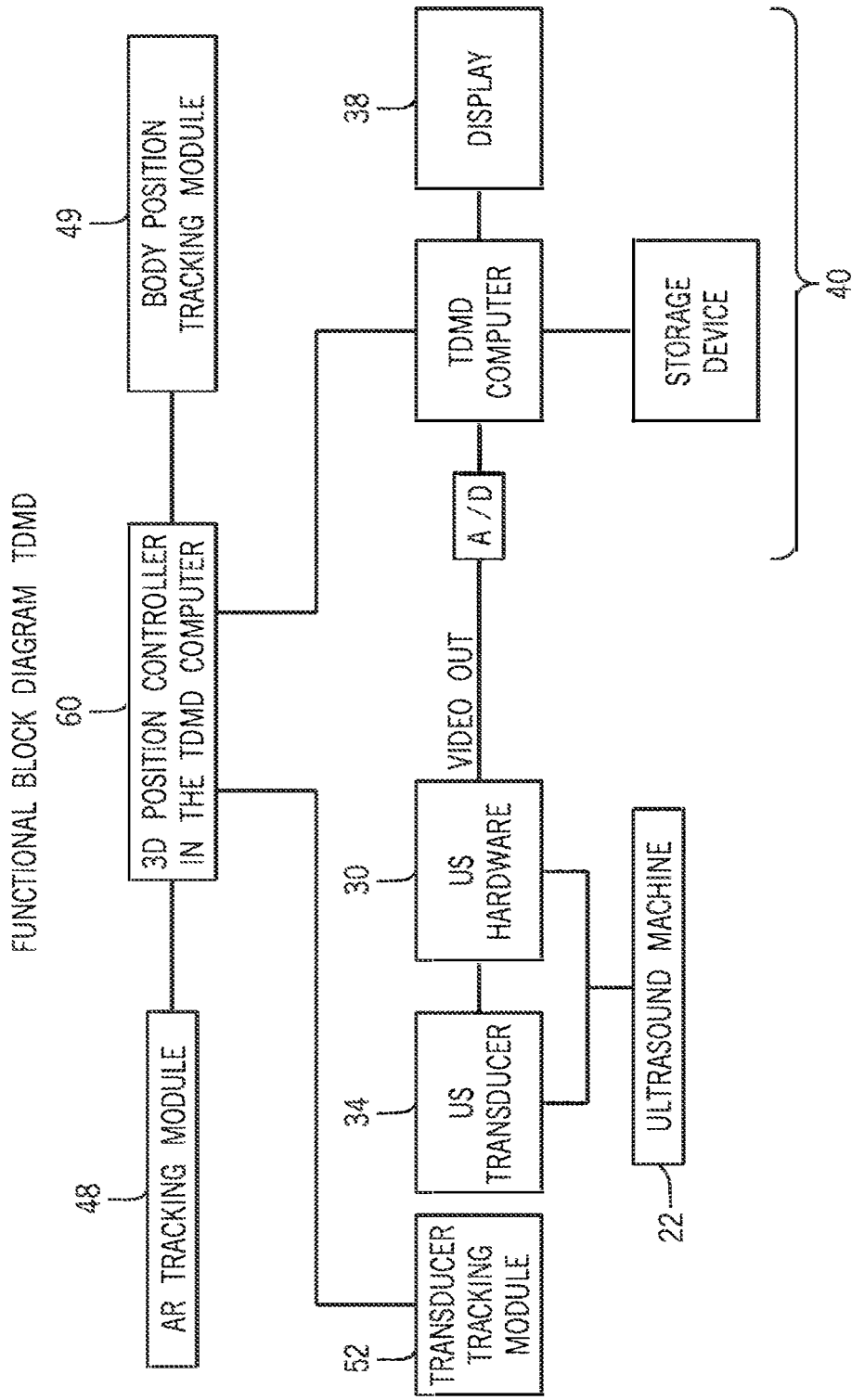
FIG. 3 illustrates the functional block diagram for the inventive device preferred embodiment with a position sensor used for anatomical reference tracking and another position sensor for body position and orientation tracking.
Figure 15:
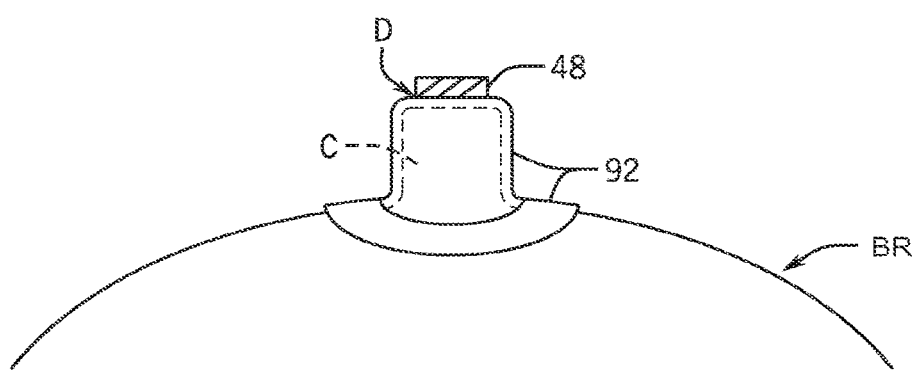
FIG. 15 illustrates a representative nipple attachment cover with a position sensor or marker.

To ensure reproducible and accurate mapping of the ultrasound images, magnetic sensors 48 and body position sensor (tracking module) 49 (FIG. 3) should be attached at well-defined and reproducible sites, outside or inside the body, during repeated ultrasound exams. First magnetic sensor 48, second magnetic sensor 52, and body position sensor 49 may be used simultaneously or singularly. It should also be noted that the TDMD could accommodate additional positional sensors as well. As a non-limiting example, in the case of breast ultrasound exam, the magnetic sensors should be attached to the Nipple C in the same position during repeated ultrasound exams. For instance, the center of the Nipple C top surface D can be the point of attachment for the anatomical reference position sensor (FIG. 15). It is desirable to have the magnetic sensor wire 54 outside the region of interest to be scanned. Continuing with the breast ultrasound exam example and with a magnetic sensor at the Nipple C, if magnetic sensor wire 54 is aligned in a direction perpendicular to the patient's coronal plane, the entire breast surface may be available for scanning, without the magnetic sensor wire in the path of the ultrasound probe 34.

To address the above, a sensor attachment device 92 (FIG. 15) may be employed to aid the attachment of a wired or wireless magnetic sensor to the Nipple C. Sensor attaching device 92 can be built as a disposable part or as a reusable part after disinfection.

Figure 4:
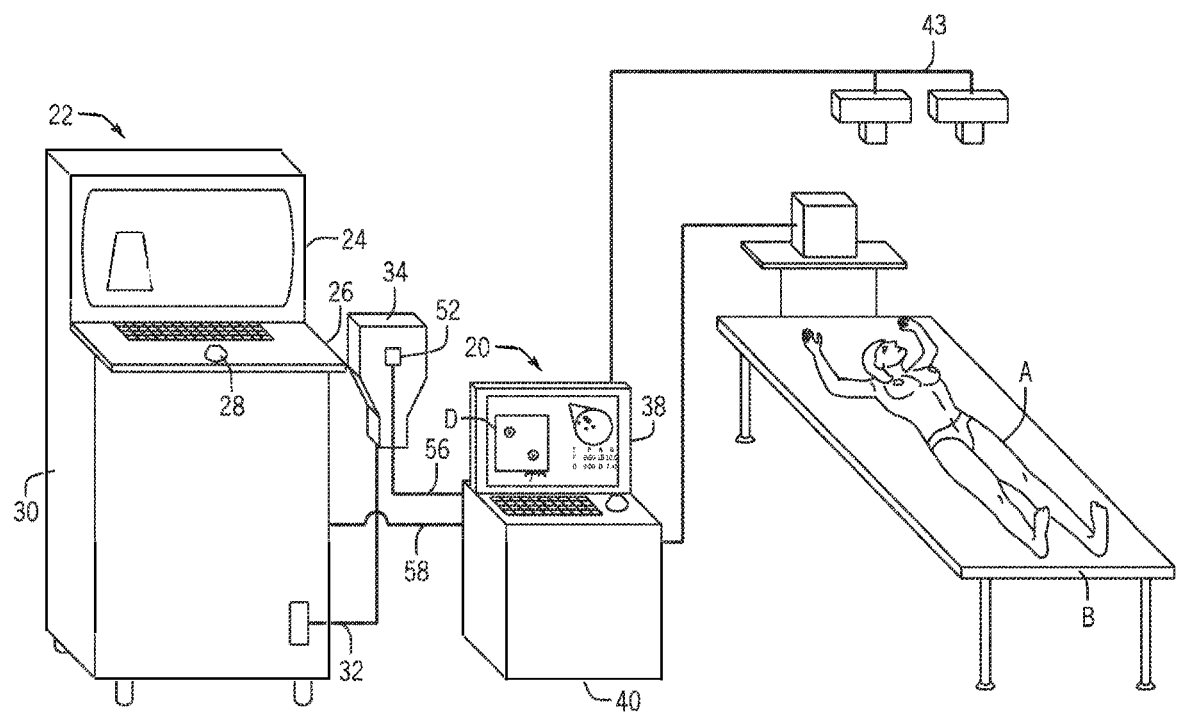
FIG. 4 depicts an alternate embodiment illustrating an overhead infrared or optical anatomical reference tracking system.

Other configurations will work as well. For non-limiting example, FIG. 4 illustrates an alternate configuration in which second optical or infrared sensor 52 provides the positional information to the TDMD 3D position board/module (not shown). The overhead infrared or optical AR tracking system 43 provides the positional information to the TDMD computer 40. Video output 24 from the ultrasound device 22 is digitized by the dedicated TDMD module/board 40. Again, analog to digital image conversion may not be required if the ultrasound device 22 can be interfaced and directly provide the digital images to TDMD computer 40. The digital ultrasound images with the associated positional information are displayed in the TDMD computer display 38 or stored for review and processing at a later time.

Figure 5:
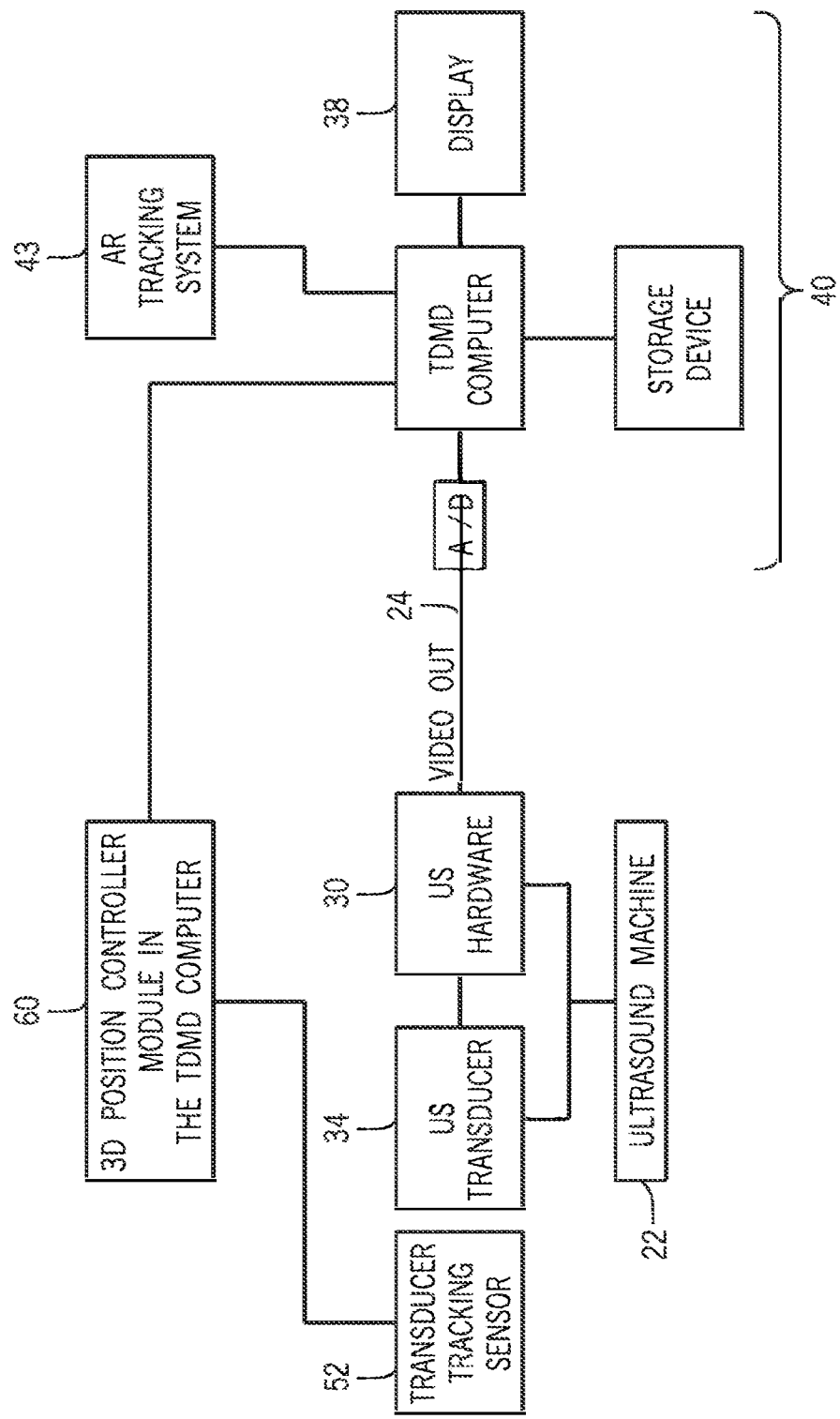
FIG. 5 illustrates the functional block diagram for the inventive device in the alternate embodiment with an overhead infrared or optical anatomical reference tracking system.

Turning to FIG. 5, a block diagram illustrating the various general working aspects of inventive device 20 are shown. Second magnetic sensor 52, which can be of any variety such as optical or infrared provides the positional information to the TDMD 20 3D position board/module 60 and overhead infrared position detector 43 transmits positional information to TDMD computer 40. Video output 24 from ultrasound device 22 is digitized by the dedicated TDMD module/board 40. It should be noted that the analog to digital image conversion may not be needed if the ultrasound machine 22 can be interfaced and it can directly provide the digital images to the TDMD 40.

Figure 6:
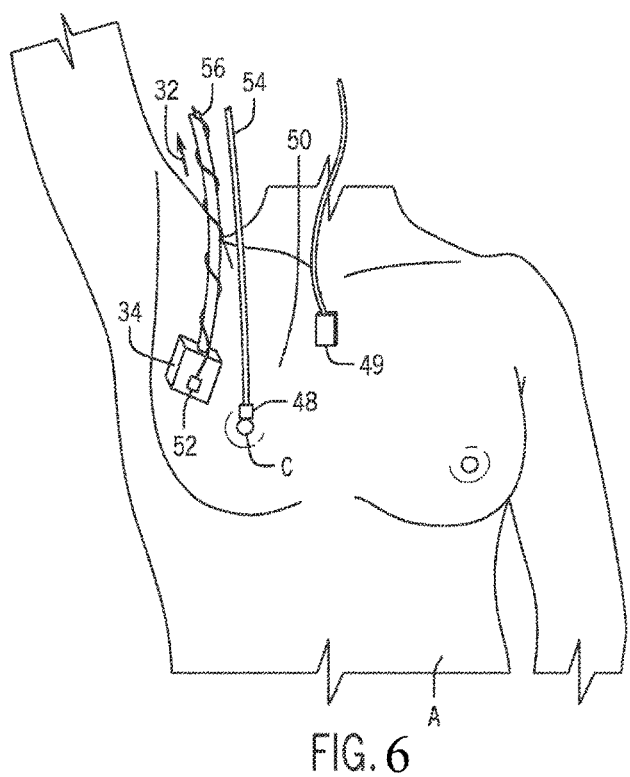
FIG. 6 depicts the inventive apparatus with sensor attached in a breast ultrasound examination

Returning to FIG. 1, second magnetic sensor 52 is attached to the exterior of probe 34 and, as seen in more detail in FIG. 6, first magnetic sensor 48 is positioned at the anatomical reference, here, the breast nipple C of Patient A.

Ultrasound device 22 video output 24 is directed to TDMD video capture board at TDMD Chassis 40 through video output cord 58 as is 3D magnetic tracking member 42 through 3D magnetic tracking member cord 46. TDMD display 38 is then enabled to shows images D captured by ultrasound device 22 and associated positional data as collected from 3D tracking member 42, first magnetic sensor 48 and second magnetic sensor 52.

Figure 7:
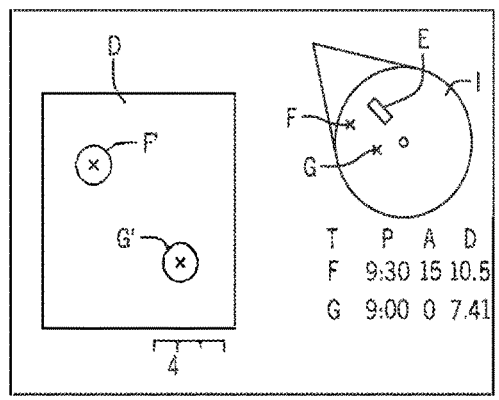
FIG. 7 depicts the image created during a breast examination as illustrated in FIG. 6.

Turning to FIG. 6, a detailed view of probe 34 with the second magnetic sensor 52 and first magnetic sensor 48 applied at the upper margin of the right Nipple C. First magnetic sensor 48 continuously tracks the anatomical reference position, the Nipple C in this case, to compensate for motion registration errors during the ultrasound exam. FIG. 7 illustrates TDMD display 38 with the captured video image D from the ultrasound machine and the body diagram of FIG. 6 with the probe 34 position and orientation at the time of image capture D and two different targets F and G in body part diagram I, and F' and G' as selected in image D image capture.

Additionally, each target is displayed with the associated position (clock face position with hourly representation or degrees to longitudinal axis and anatomical reference as center) and distance (cm) from the selected anatomical reference. Positional coordinates are displayed under body part diagram I in FIG. 7. While the inventive device can enable any number of coordinates to be displayed, here the example includes Target number (T), example F and G, Position in reference to anatomical reference in hourly format (here, 9:30 for F and 9:00 for G), position from anatomical reference in degrees (here, 15° for F and 0° for G), and distance from anatomical reference in centimeters (cm) (here, 10.5 cm for F and 7.41 cm for G). When anatomical reference sensors 48 and 49 are used to dynamically track the position of the nipple and patient's body, the clock face position can be calculated in reference to the real time patient's body orientation planes, which would increase the accuracy and reproducibility of measured targets positional coordinates FIGS. (3, 9). Also, probe 34 is identified at transducer position Icon E for its position location and orientation.

Figure 27:
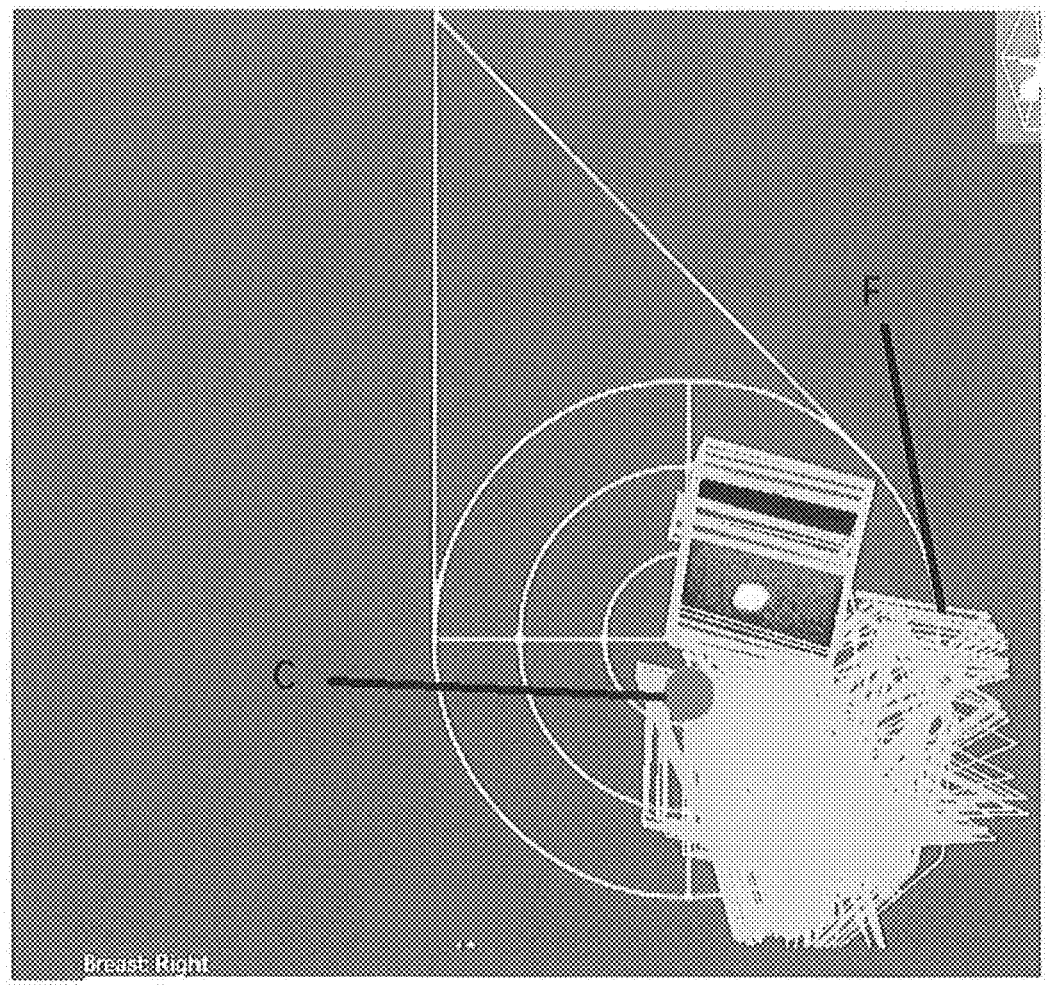
FIG. 27 is an example of the display of multiple ultrasound probe and frames positions over a body diagram.

An additional function is to display a cumulative area of the transducer positions (via icon E) over the body diagram, where the ultrasound images of breast tissue were generated and displayed in real time, during patient examination. FIG. 27 displays all ultrasound frames generated while scanning the breast (F) over the breast diagram with nipple C. This will allow for a quick evaluation of ultrasound examination completeness and demonstrate the region evaluated by the operator. The display of cumulated frames position and orientations can be done at the time of the examination or at a later time. A more detailed description is following in this patent application.

In the preferred embodiment, any off the shelf generic PC computer with Windows XP®, Windows 7 (by Microsoft Corporation, Redmond, WA) can be used to run instructions compiled in C++ and dotnet languages. While preferred, those skilled in the arts will understand that the invention can be implemented on any other computer platform and operating system.

The software substantially used to process the data received by the processor from the at least one sensor and data from the ultrasound to manipulate the data for identifying, and storing in memory as selected by the user, target site location and size information in relation to selected anatomical reference(s) for simultaneous review and interpretation and later retrieval for comparative purposes with later examination, whether compared in real time or a later time based upon saved data. The inventive device enabling a user to accurately review, evaluate, and compare examination results by having anatomical reference(s) guides to isolate target sites.

The body diagram representation is not limited to the "bird's eye view" type like the "clock" representation for the breast, but more complex and realistic three dimensional representations of the body or body regions, including images obtained with other modalities like MRI, mammograms, gamma cameras or positron emission tomography and using contour rendering algorithms, can be used. The calculated and recorded positional data can be displayed in these representations. The ultrasound transducer position, orientation, can be depicted in a realistic appearance in space so it can be easily reproduced at subsequent examinations.

Additionally, the preferred 3D position registration system is based on magnetic tracking technology (for example, like that manufactured by Ascension Technology, Burlington, VT); however, any other suitable technology, such as optical or ultrasound, may be employed. Moreover, the inventive device can be deployed as an add-on to any existing ultrasound unit, and can outfit DICOM compatible and non-DICOM machines as well. The infrared sensors, also commercially available (Natural Point Inc., Corvallis, OR), comprise at least one infrared camera with the dedicated hardware and software receiving reflected infrared light from the reflectors or emitted infrared light from small infrared light sources applied over the anatomical references. The infrared cameras can be replaced with optical cameras and the infrared reflectors or emitters with optical markers or light emitters. One or more infrared or optical cameras can also be used.

The ultrasound probe and anatomical reference point real time tracking is not limited to the above solution, but other tracking modalities like ultrasound, optical, inertial etc. can be used for the ultrasound probe and optical/pattern recognition, magnetic, etc. for the anatomical reference point real time tracking. It should also be noted that tracking modalities can be used in combination with one another, for non-limiting example, ultrasound tracking with optical tracking. It is also notable that the described TDMD system and method can optionally be used with the anatomical reference tracking feature disabled.

In any of the above configurations, initial calibration is needed to register the ultrasound probe scanning plane orientation and position. Any 3D calibration method for 2D ultrasound probes, as available in the published literature can be used.

The position of a small tumor or other target in the breast, or other body part, depends on the patient's body position due to the gravity effect, ultrasound probe position and orientation which can displace the tissue under the probe and the pressure applied by the operator on the probe. To obtain accurate reproducible positional coordinates of a lesion, the above conditions need to be measured and able to reproduce at a subsequent exam.

Figure 11:
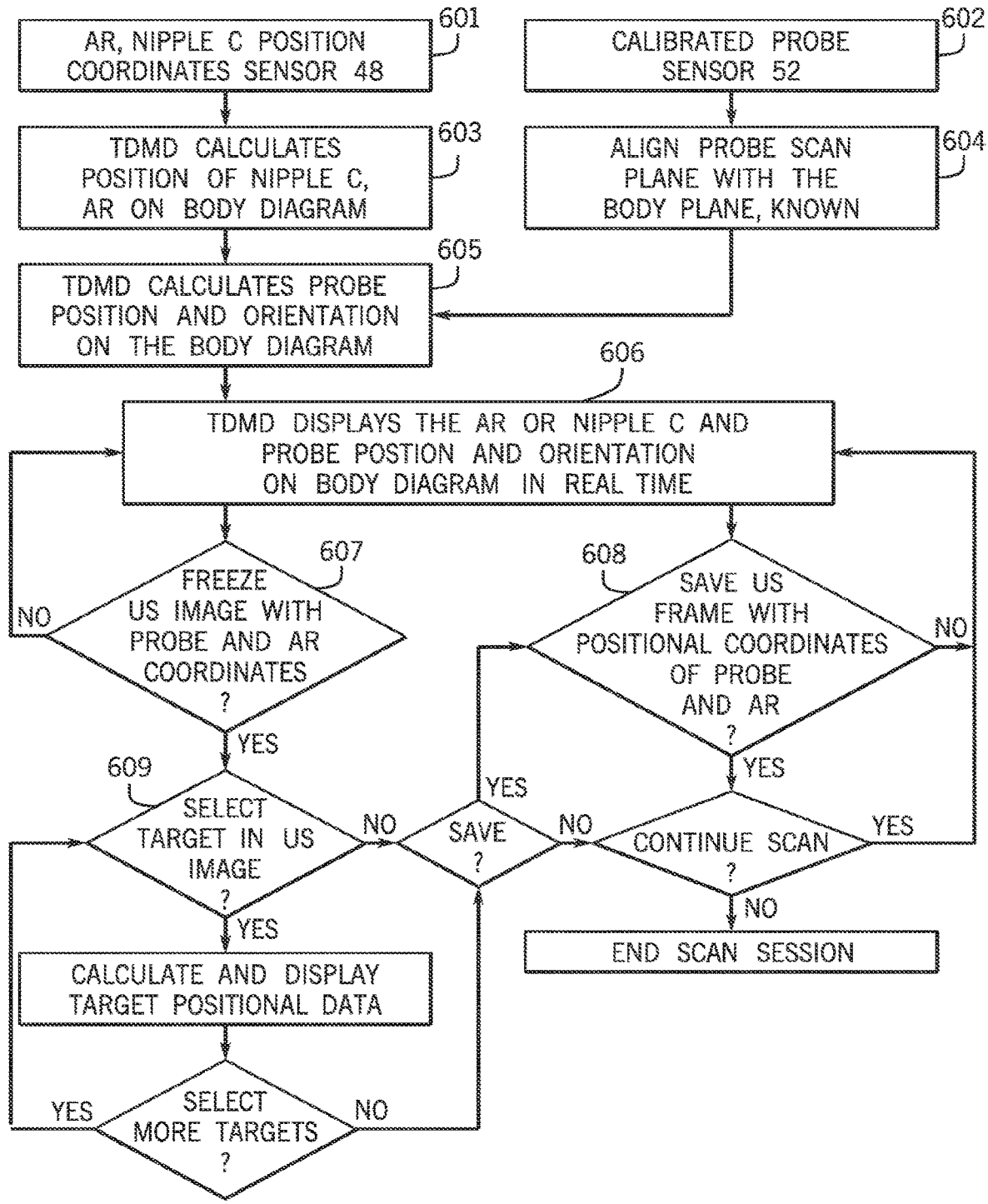
FIG. 11 illustrates one method of patient's body planes registration and the steps needed to calculate, display and record the positional information associated with the diagnostic ultrasound images with a position sensor used for anatomical reference tracking and another position sensor for body position and orientation tracking.

Turning to FIG. 8, the TDMD operation steps required to record the 3D position of targets in relation to anatomical references are shown. For each patient, at the beginning of examination the anatomical reference spatial position, patient's body position and the ultrasound probe position relative to anatomical reference(s) and its orientation relative to the body anatomical planes are defined in a spatial coordinate system and recorded, (FIG. 8, 501). This step provides the reference for the coregistration of the ultrasound probe and images with the body diagram or secondary set of body images. One method is to hold the ultrasound probe scan-head center at the anatomical reference, for example, on the Nipple C, with the probe 34, fitted with position sensor 52, held in a known orientation with the patient's body planes and axes, for example sagittal plane, horizontal, parallel to the patient and examination table long axis (FIG. 1) to determine the patient's position and orientation axes and planes. In this step the nipple C position is set with the position coordinates at the center of the probe and the known patient's plane, sagittal for example, is set using the coordinates of the probe scan plane. This method does not provide dynamic positional tracking for nipple C and patient's orientation planes, therefore patient motion will likely lead to position registration errors in the ultrasound images. At least one anatomical reference needs to be defined at the beginning of each examination, however more than one anatomical references can be defined, which can increase the measurements accuracy. During the anatomical reference setting step and during scanning a second magnetic sensor 52 is used to track the ultrasound probe, the first magnetic sensor 48 position attached at the anatomical reference (nipple C) is recorded and computed by the TDMD 40, so it can continuously track the anatomical reference. In this configuration with 2 sensors, (52 and 48), the nipple C position coordinates are obtained from sensor 48 and only the patient's body planes needs to be set, for example by holding the probe with the scan plane parallel with a known patient's plane and set the patient orientation planes (FIG. 11). This method provides the dynamic referencing of the nipple C or other monitored anatomical reference but is limited due to the static referencing of patient's orientation planes. A method where the patient's body orientation planes are dynamically referenced is described below.

An additional calculation provides the offset between the anatomical reference point and first sensor 48 position and is necessary when the first position sensor 48 is applied in close proximity, but slightly off the selected anatomical reference. This is a non-limiting method to measure and apply the positional offset between sensor 48 and an anatomical reference point. In other embodiments with wireless anatomical reference sensors or markers, for example when using the overhead anatomical reference tracking system with infrared or optical sensors or markers, are applied exactly at the anatomical reference point, this additional correction is not necessary and can be omitted. If a wired anatomical reference marker can be applied exactly at the anatomical reference point, this additional correction is not necessary and can be omitted.

During an ultrasound exam, the patient's body position and orientation can change, which can have an effect on the measurement and description of a lesion's position. During the real time ultrasound exam image acquisition and capture, each internal ultrasound target position relative to the anatomical references depends, among other factors, on the patient's position relative to the direction of the gravity force or the earth's magnetic field. Therefore the positional relation between the patient's body position and an examination table, B or other reproducible fixed reference used to position the patient, a chair or a wall for example, can be associated with the ultrasound images or other images of the body, to aid repositioning the patient at subsequent imaging and match the gravity force effect between temporally distinct image sets. The gravity force effect is larger on deformable structures, like the breast. For example, during a breast ultrasound exam, the position of a small target in the breast relative to the nipple or other anatomical reference can change between the supine and half decubitus patient positions on the examination table. Unlike the approaches of the prior art, at the follow up exams or during the same patient exam, the patient whole body position can be adjusted to match the body position relative to the examination table or other known fixed reference object recorded with the previously obtained ultrasound images and help finding a target with the previously recorded coordinates relative to the same anatomical references.

The examination table, B, or other reference object with known position is registered in the same spatial reference frame with the ultrasound probe and images and patient's body position. The first set of images which can be the ultrasound images are coregistered with the second set of images which can be the patient's body diagram and which can be coregistered with a third set of images which are of the examination table, B, or other object with a reproducible position related to the gravity force direction. The coregistration of the three sets of images can be performed dynamically for all image sets, with positional sensors or markers providing continuous or quasi continuous output or a combination of dynamic and static registration, where one or more anatomical references are dynamically tracked at the body and the examination table or third set of images position can be tracked with dynamic sensors or spot measurements if fixed in the spatial reference frame during the ultrasound exam, like an examination table (FIG. 12) The examination table B position can be determined and saved for future use in the spatial frame coordinates, if permanently aligned with the spatial frame or can be dynamically determined with a position sensor attached to the table if the table moves in the spatial frame. Examples of compatible spatial reference frames include magnetic, optical, infrared, ultrasound or combinations of two or more types of positional reference frames with the corresponding transmitters and sensors or markers. The coregistered sets of images can be displayed together or separately, temporally synchronized or not synchronized. Also, it is possible to display at same time coregistered sets of images of same body region obtained at different times, to facilitate the image comparison process for diagnostic and treatment purposes.

Figure 28:
FIG. 28 is an example of ultrasound frame displayed over a body diagram aligned with the body planes.

The patient's whole body position and orientation representation, BO, examination table, or other fixed reference object position and orientation, B, position and coordinates of Nipple, C, position and coordinates of a target, T, position and orientation of the ultrasound image, E, position of sensor 49 on body, S, can be recorded with each 2D ultrasound frame FIG. 28. The above positional representations and corresponding alpha numerical values can be displayed and recorded in any combination or order.

There are multiple methods to align the patient's body planes and axes with position sensors and an exam table or other objects.

A preferred embodiment describes a nipple sensor for nipple position tracking 48, and a body position sensor which can be attached to the sternum or other body part 49 and connected with above described apparatus and system.

The patient's whole body position recording can be automated in the TDMD by tracking and recording the position coordinates of the anatomical reference sensor or sensors attached to the patient's body and compared with a reference body position coordinates.

Figure 10:
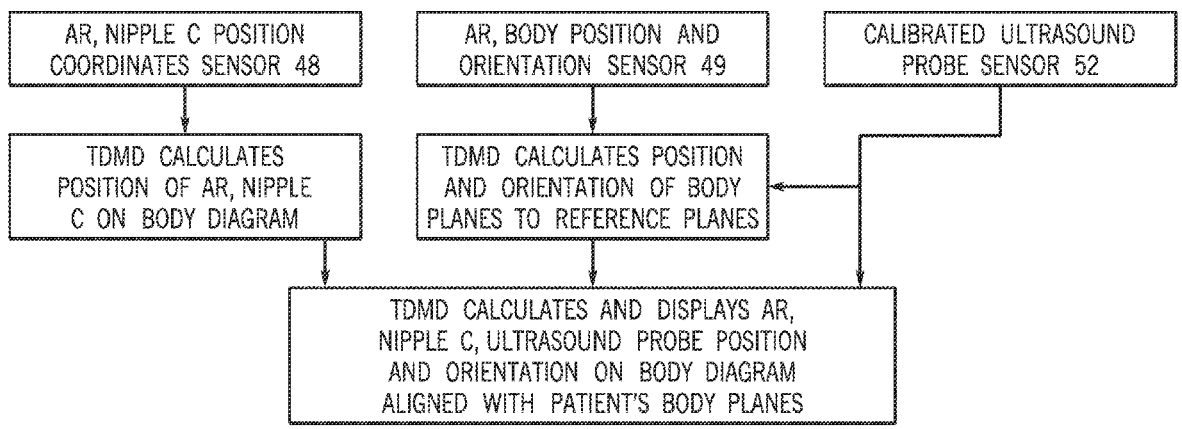
FIG. 10 illustrates the steps needed to calculate, display and record the positional information associated with the diagnostic ultrasound images with a position sensor used for anatomical reference tracking and another position sensor for body position and orientation tracking.
Figure 12:
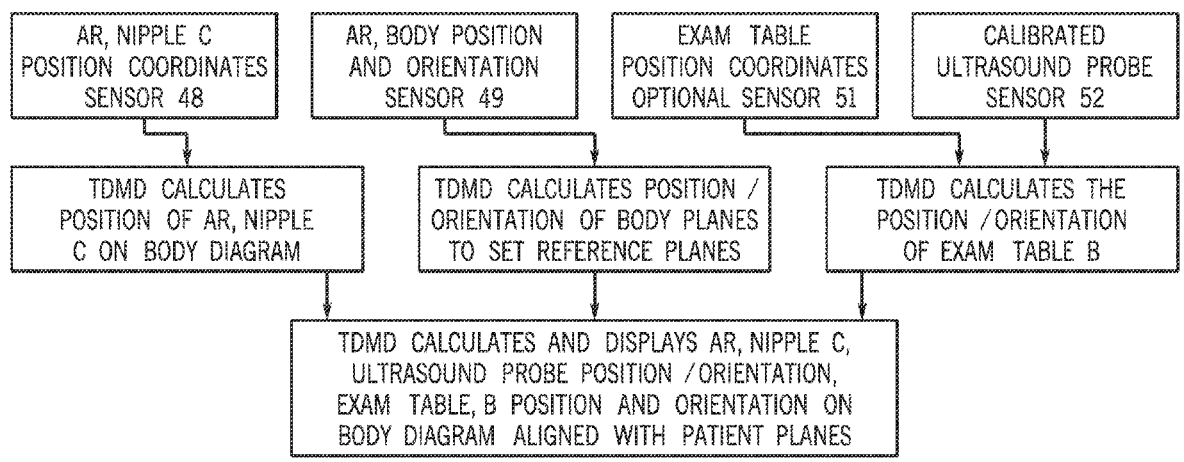
FIG. 12 illustrates the steps needed to calculate, display and record the positional information associated with the diagnostic ultrasound images with a position sensor used for anatomical reference tracking, another position sensor for body position and orientation tracking and exam table position input.

In one embodiment, with the patient's body in the supine or other known reproducible body position on an exam table, B, body position sensor 49 attached to the patient, the output from the position sensor 49 can be used to measure and set the body reference position and orientation in the TDMD, associated with the known patient position on table. The patient's reference body planes or axes can be set to match the known exam table axes or any other known orientation planes, including the probe scan plane when aligned with one or more of the patient's body planes and axes (FIGS. 10, 12). After setting the patient's body reference planes in the spatial frame, the output from body sensor 49 can measure changes in the body position and orientation during the imaging session. The patient's body position can be represented as the 3 orthogonal imaginary axes and planes used to represent the whole patient body position, coronal, sagittal, axial (BO, FIG. 28) or any other conventional representation. The patient's whole body position relative to the examination table or other fixed reference object can be recorded for each 2D ultrasound frame.

A limitation of this method of body position determination is that it requires setting the reference patient position with each exam or image acquisition session. Changes in patient reference position between different imaging sessions may result in patient's body positioning differences and calculated coordinates and display errors, therefore careful positioning on the exam table in the same reference body position is required with each imaging session to maintain an acceptable reproducible accuracy.

In another embodiment, the patient's planes and axes can be measured using multiple anatomical references with the patient's body holding in one position and orientation on the exam table. For example, longitudinal and transverse axes of the patient can be initially determined by recording the position of the sternal notch, the xiphoid process of the sternum and both acromial processes at the shoulders and calculating the longitudinal and transverse axes in reference to the exam table or other fixed object, respectively. The reference planes and axes positions and orientations are associated with the body reference sensor 49 and changes in the patient's body position and orientation can be calculated and displayed.

Alternatively, with the patient's body in any position related to the exam table or other reference object, one or more reproducible anatomical references can be selected to generate a line, plane or volume with an known shape and position to the exam table. The anatomical references position can be measured once, at time intervals or continuously, when a position sensor is attached to one or more positional references. The position of body axes and corresponding planes can be calculated and displayed in reference to the exam table or other fixed object position, when their position is known in same positional reference frame.

The body position measurement alignment can be further simplified when the body position sensor 49 is attached to a body attachment part that allows the positioning and attachment of the sensor 49 in the same position and orientation at repeated imaging sessions separated in time. The body attachment part is designed to be aligned with the patient's body planes and axes and follow their position and orientation changes. The body attachment part 60 with sensor 49 can be calibrated with the body axes and planes and attached at a reproducible anatomical reference, the sternal notch for example (FIG. 6). The body position sensors output is registered with the positions of above measured axes, planes or volume positions and the changes in sensors output are used to calculate the patient's body axes or planes positions changes which can be displayed in reference to another reference object, like the exam table. The positional data obtained as described above can be used to determine the patient's body position at the beginning and during the exam. The reference axes and planes can be determined at any time during an exam, once or more times and used to calculate the patient's body position changes during the exam, when the body position sensors outputs are recorded with the recorded images or instantly calculated and displayed during ultrasound scanning.

Figure 29:
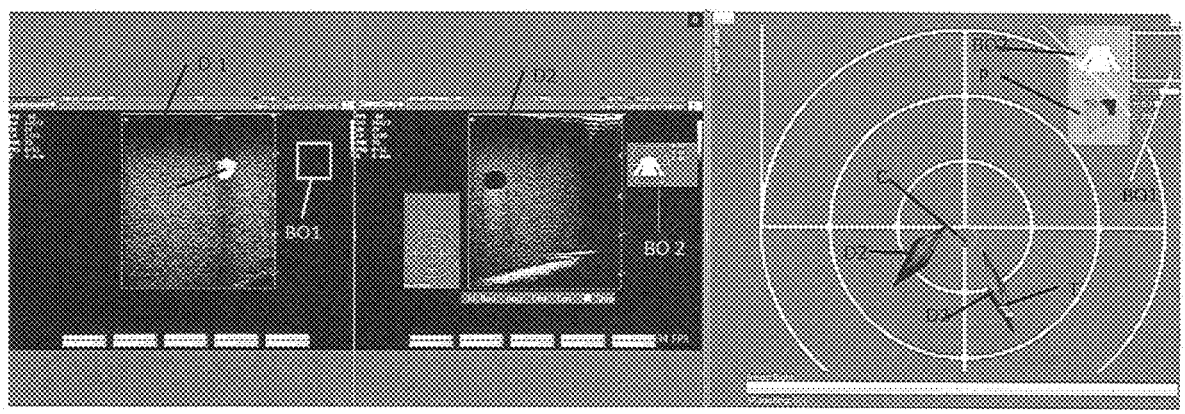
FIG. 29 is an example of a target relocation screen with multiple guides for probe frame, target and body position/orientation relocation.

The rotation around the initial position of axes and planes can be graphically represented and recorded. The recorded body position from a previous exam image or images can be displayed at the same time with a subsequent exam real time images and used to reposition the body in the same position the previous images were obtained, to help produce the images in the same orientation and directions as those of previous images and help the relocation of previously detected targets and other associated findings with known positional coordinates relative to the anatomical references (FIG. 29).

Figure 13:
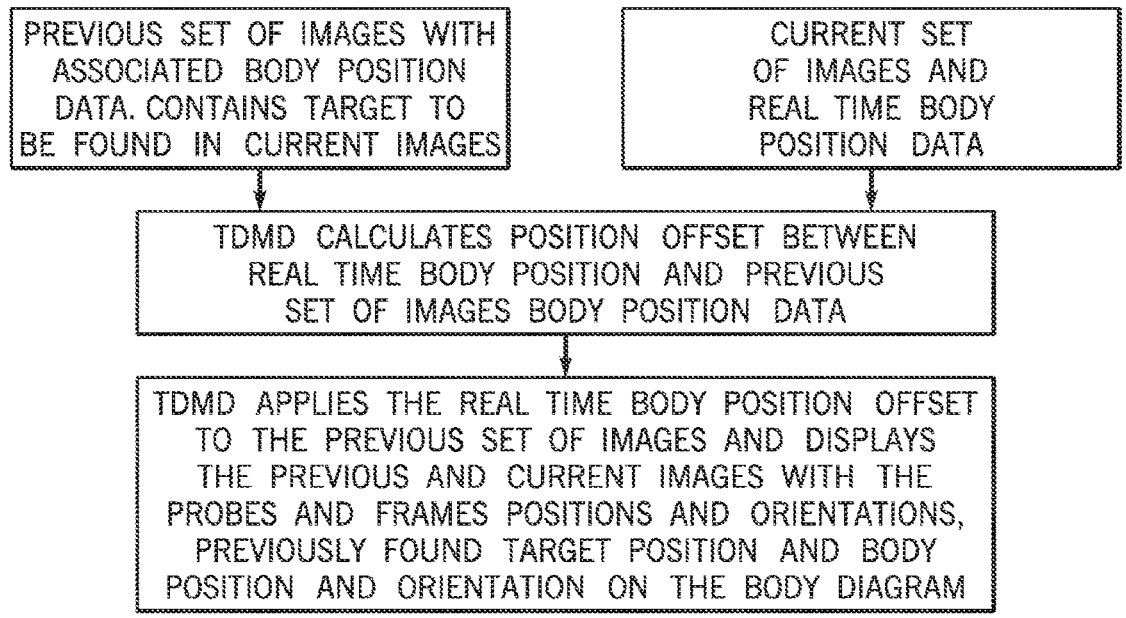
FIG. 13 illustrates the steps needed to calculate the positional offset between the body position and orientation in 2 temporally different image sets, apply and display the calculated data over a body diagram.

Furthermore, during ultrasound scanning, if differences exist between the body position recorded with the previous images of same body region, the positional difference can be applied at the previous, set of images to adjust the previous set of images positional data and display to guide the operator to match the real time images, with the previous set of images (FIG. 13). This method can be applied with a set of old images and current images during scanning or to multiple sets of old images to realign image sets recorded at different times. One limitation with this realignment method is than does not account for the gravity effect on the body tissues and would work better for targets in solid organs, like liver, which would not change much the position relative to body with body position changes.

Figure 19:
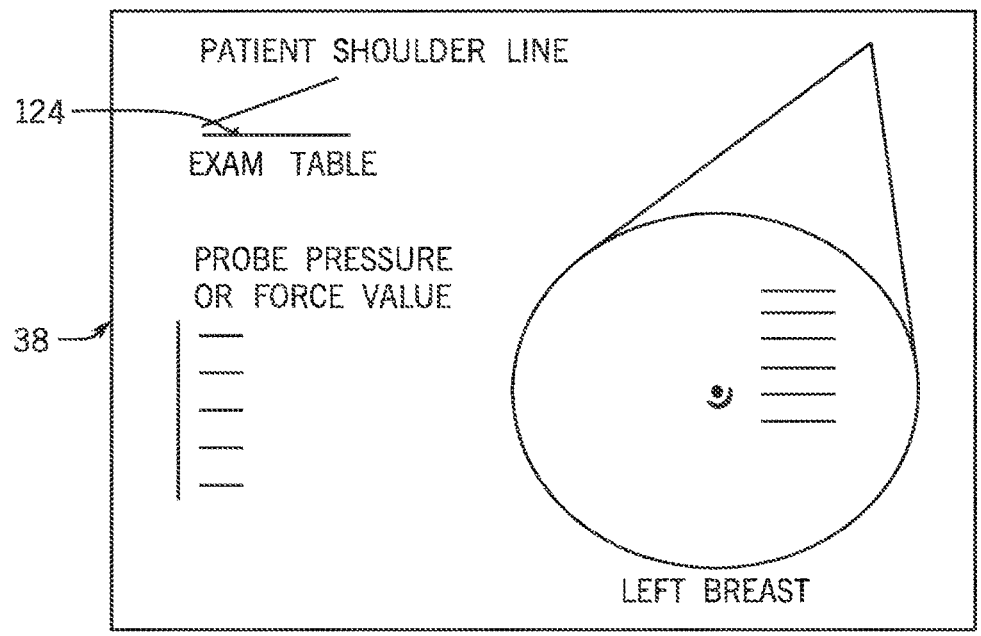
FIG. 19 depicts a display screen shot illustrating patient position with respect to exam table and corresponding body diagram with ultrasound frames.

With any method used for the patient's body position tracking, during the ultrasound examination, the positional change output from the reference sensors on the patient is applied to calculate the patient's planes position and orientation, and recorded with corresponding ultrasound images. The real time or recorded images can be displayed with the corresponding body position relative to the exam table or other object together with the body diagram used to represent the ultrasound probe, scanning plane, body part map and the recorded targets (FIGS. 19, 28). It is understood that any other method to determine the patient body position and orientation relative to the exam table or other reference fixed object, at the beginning or during the ultrasound exam, can be used and the positional changes from the sensors attached to the patient are applied to the patient body coordinates to display the whole body position change relative to the exam table or other fixed reference.

In another embodiment, the TDMD apparatus with 2 or more position sensors can have a pressure sensor attached at the ultrasound probe head to record the pressure applied with the probe to the tissue with each image and during scanning. An alteration is to attach a force sensor to the probe with an attachment mechanism to record the force applied to the probe and in turn to the tissue. If a force sensor is used in this fashion, the pressure at the probe head that applied to the tissue will be obtained by the force reading divided by the area of the probe head surface that comes in contact of the skin. The pressure values recorded with each ultrasound image can be available during subsequent scanning of the same area and can guide the operator to apply a similar pressure to increase the images reproducibility. The probe pressure values can be displayed in alpha numerical form or graphically next to other probe indicators for position, orientation, speed and others (FIG. 19).

Figure 31:
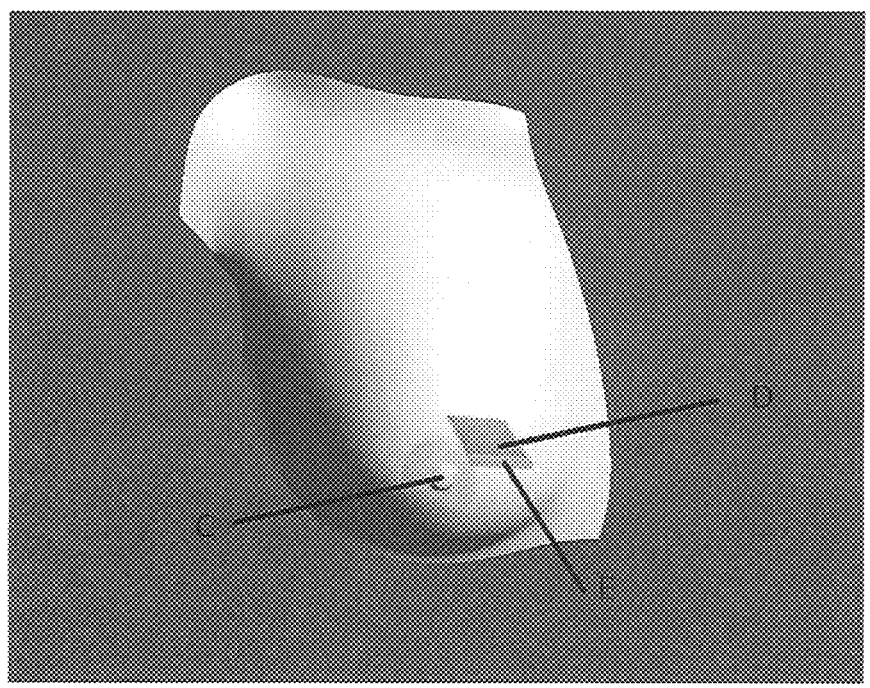
FIG. 31 shows the ultrasound frame displayed over a realistic body diagram.

Continuing with FIG. 8, at 502 the probe 34 position and orientation and anatomical reference are continuously displayed in TDMD computer display 38 or ultrasound display 24, as a moving icon, E or the actual ultrasound frame D over the body part diagram or other representation, in relation to one or more anatomical reference(s), nipple C or others (FIG. 31).

Figure 14:
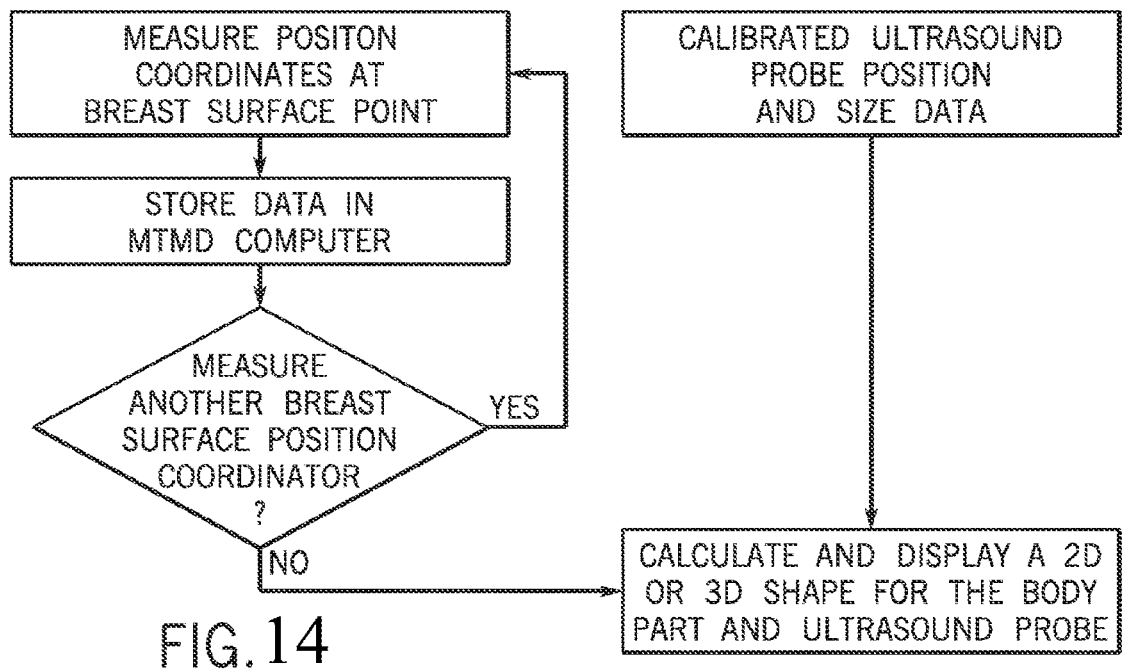
FIG. 14 illustrates the steps needed to calculate and display a realistic same scale representation of a breast with the ultrasound probe and frame position and orientation.

For a realistic representation of the body map and ultrasound probe icon and frame at the same scale, the body diagram or other body representation can be calibrated to match the ultrasound probe size. In one non limiting example the radius of the breast can be measured and used to calculate the size of the body diagram at same scale with the ultrasound frame representation. In another non limiting example, the position coordinates of multiple points at the margins of the breast or other structure can be measured and used to fit a 2D or 3D shape of the breast or other structure to be used as the body diagram with the TDMD display (FIG. 14).

When knowing the real size of the body part, the probe position can be accurately tracked to the body surface and determine when the probe is outside the scanning area or volume. With the described feature, an "out of range" warning can be issued when the probe is moved out of the scanning region range or too far from the spatial frame used to track the sensors.

The frame images are entered and displayed in the TDMD display 38 or if implemented at the ultrasound machine host computer, ultrasound display 24. In the preferred embodiment, the ultrasound user can "freeze" the 2D still image of interest or capture video cine loops or 3D images (FIG. 8, 503). The "frozen" image or the video clip can be saved in TDMD computer 40 or a host computer with the positional information associated to each frame or set of frame images, in a local database 504 (FIG. 8).

The coordinates associated with a target in a still image, in relation to anatomical references, can be displayed by pointing to the target (image pixel/region of pixels) with a pointing device in the image displayed on the TDMD display 38 or Ultrasound display 24, step 505 (FIG. 8). The target position can also be determined at a later time in the same TDMD computer or a remote computer with the TDMD software, from the saved ultrasound images with the associated positional information. The target positional information can be displayed at the time of the ultrasound examination or at a later date, and it also can be printed and stored in digital format at any time after the acquisition.

For the images in cine loops, the position display process is similar to the still images, after the cine loop is "frozen" at a certain frame. For 3D ultrasound probes, the same principle applies when a 2D image is reconstructed from the recorded 3D data and the positioning information is applied to the reconstructed ultrasound 2D image.

Also, each voxel in the volumetric image set has associated positional coordinates calculated using the position sensors outputs and therefore the position coordinates of each selected voxel or voxels can be accessed and displayed.

The position of each pixel in an ultrasound image or voxel in the volume images in reference to the anatomical reference(s) is calculated from the ultrasound probe tracking system data and corrections applied to the anatomical reference(s) from the secondary tracking system that monitors the anatomical reference(s). Both tracking systems provide 3D positional data. The positional information displayed for each image is presented in alphanumerical format as distance and angle from the anatomical reference, hourly or clock face position coordinates, where the position of a target is assigned an hour from 1 to 12 o'clock, clock face position, when the region (breast or abdomen) is viewed from above as a clock, with the anatomical reference, Nipple C or umbilicus respectively, imagined in the middle of the clock and also as a graphic diagram of the region, see, e.g., FIG. 7. Additional data fields are also available, including the position of the patient during the examination (supine, lateral decubitus, or any other position, etc.).

The clock face position can be calculated to represent the projection on the patient's real time coronal plane, as determined from the body position tracking module. The graphic diagram points to the relative position of a target over a diagram of a body part, the breast, for example. Accordingly, it is easy to see that multiple targets can be selected/displayed or erased.

The TDMD computer allows for the manual or automatic entry and display of target coordinates from previous exams over the body diagram or body part diagram, with the ultrasound probe icon position and orientation in relation to the anatomical reference(s) and body axis, represented in real time in the diagram. This feature allows for ultrasound device operator orientation and guidance to help moving the ultrasound probe and find and examine a known target from a previous examination.

Figure 37:
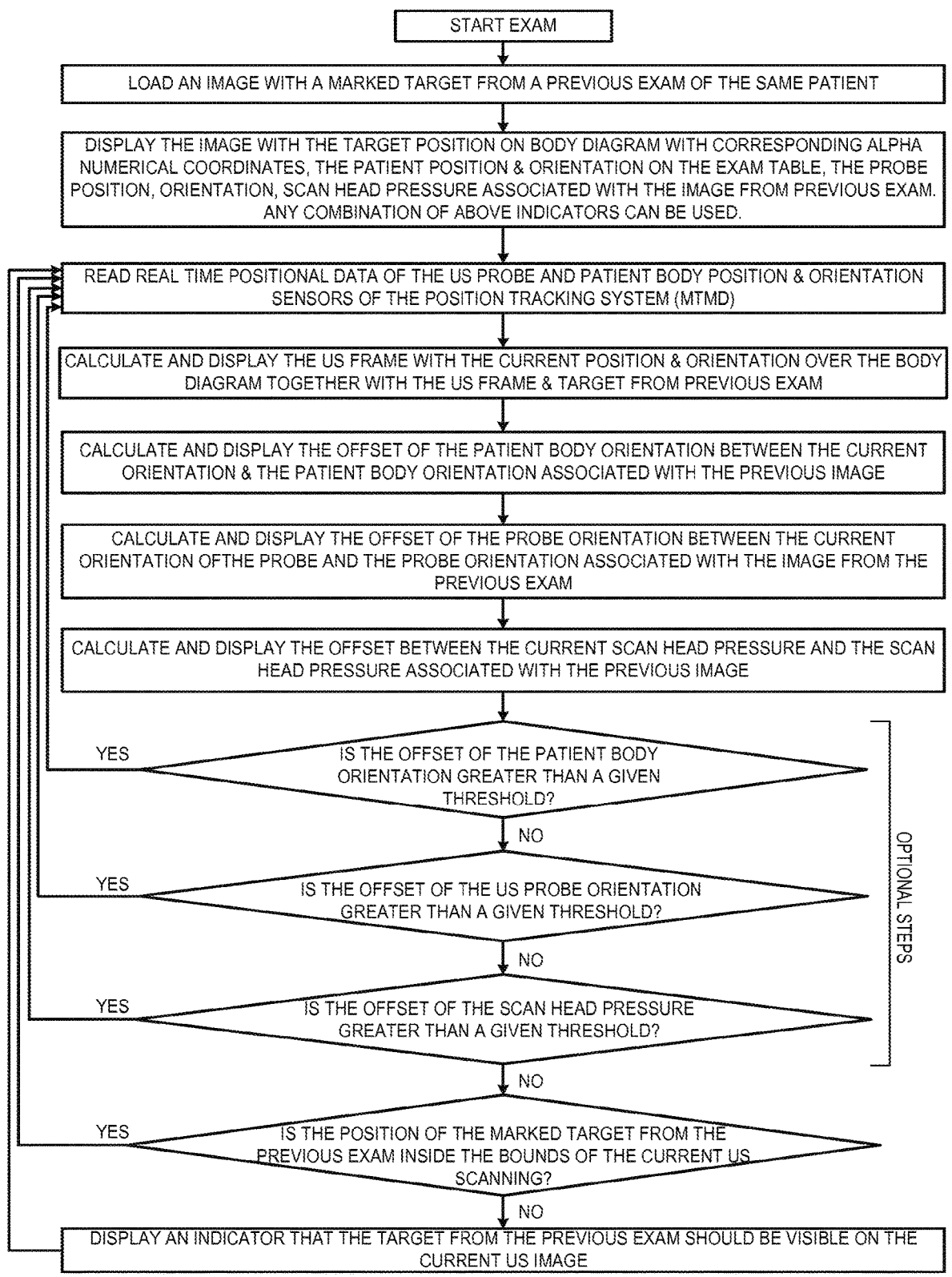
FIG. 37 shows the steps required to relocate a target from a previous ultrasound exam.
Figure 38:
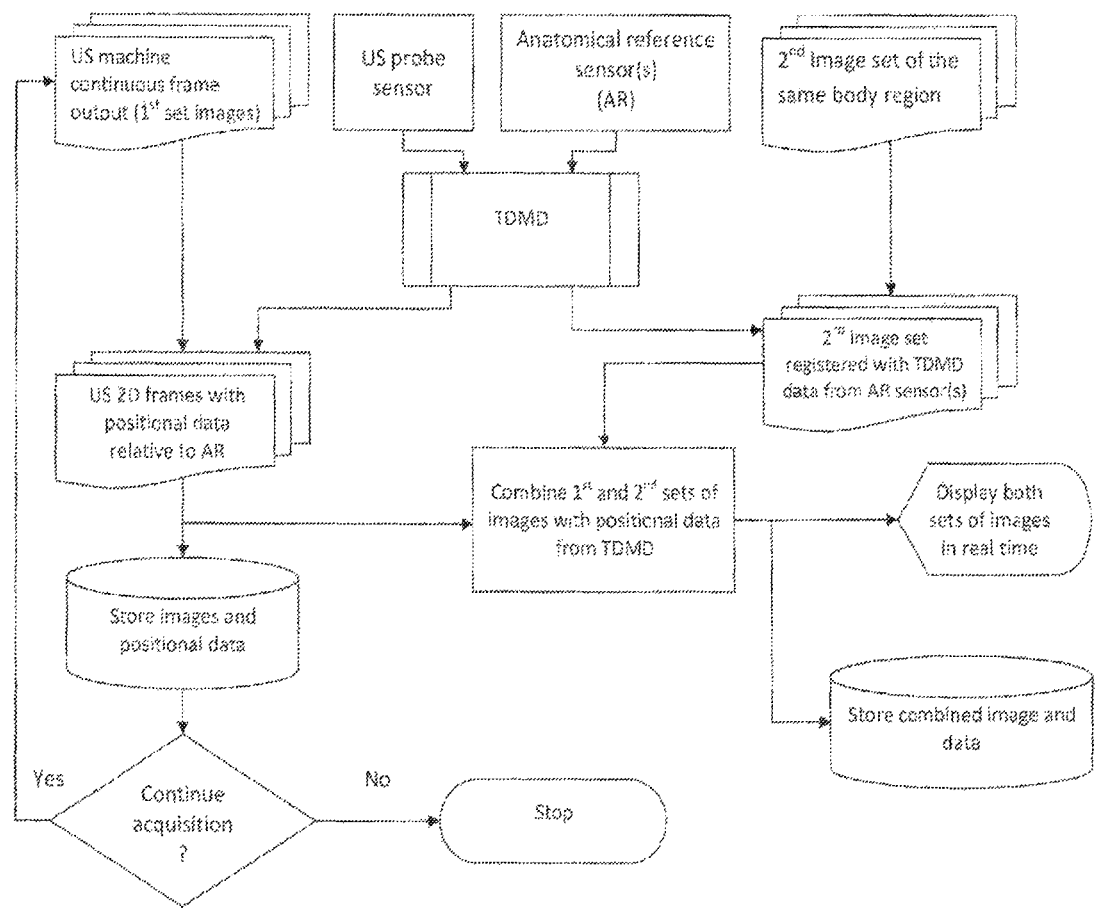
FIG. 38 shows the steps required to coregister real time ultrasound images with a second set of images of same body region.

Also, to help finding a previously recorded target with known positional data relative to the anatomical references, ultrasound probe position and orientation and depth from the scan head, the previous and current real time data described above can be simultaneously calculated and displayed for real time guidance during a repeat ultrasound scan (FIG. 37).

A method of assisting the ultrasound operator to re-locate previously examined target in a follow-up exam is described.

In a follow-up exam, it is desired to examine the target of interest in the same probe location and orientation as in the initial exam. It is also desirable to match the patient's body position in the current and previous exams, more important for deformable structures like the breast. Therefore, a method that can guide the operator to navigate to the same probe location and orientation is of great interest.

The relocation navigation method for the ultrasound probe consists of two components, translation and rotation of the probe, helping to achieve imaging the target of interest at the previously recorded location and viewing angle, respectively. The ultrasound images with relocation guides are shown in FIG. 29.

For the translation mapping, on a 2D or 3 dimensional (3D) graphic display of the body part (breast, liver, etc.), a previously recorded ultrasound image that contains the target of interest T (first image) is displayed with its location and orientation defined from the positional data saved from the previous recording. Its positional representation is referenced with the positional coordinates from the anatomical reference sensors applied at the same landmarks as in first image acquisition.

On the same 3D graphic display of the body part, the current probe position together with the real-time 2D ultrasound image D2 is displayed in real-time (second image) with the position dynamically referenced to same anatomical landmarks as with the first image. Because the first D1 and second D2 images and probe position are displayed in real-time and dynamically referenced to the same anatomical landmarks, moving the probe will change the location of the displayed probe position and the real-time image relative to first image. As the operator moves the probe over the body part, the second image is moved along with the probe. In this way, the operator has a visual guide to move the probe closer to the probe position where the first image was recorded, and eventually achieved the same probe position as that of the first image (FIG. 29).

Beside the 3D graphic display of the body part, a graphic indicator of probe rotational orientation with regard to the 3 anatomical planes (coronal, transverse, and sagittal) is displayed. This graphic indicator for probe orientation can be of a gyroscope type or any other type that describes the rotational orientation of the probe.

With the graphic indicator, the orientation coordinates of scan plane orientation in the first image with the target T, D1 and scan plane of current image, D2 are displayed.

Around the 2D first ultrasound image D1, there are 3 rings, axes or planes centered at this image, representing rotational orientation of the probe in coronal, transverse, and sagittal plane in real time, respectively. Alternatively, the scan in first image D1 and second image D2 can be displayed, P.

When the probe is rotated in any of the three anatomical planes, the ring indicating the probe rotation in this plane will spin accordingly in real-time with the same degree of rotation that the probe is rotating in this plane.

When the probe is rotated in the same probe orientation as the first image, it is expected that the three rings, axes or planes will be in the same plane, as shown in the figure. Any other graphical or alpha numerical indicators can be used to guide the user in matching the 3D orientation of the probe during second image acquisition with first image.

The patient's body position and orientation on the exam table can be displayed together with the body region diagram or separately. The body position indicators associated with the first exam image, BO1 can be displayed together with the body position indicators with the second or current exam BO2, to guide the reposition of patient's body to be in the same position as with the first or previous exam.

When probe pressure over the tissue is recorded with images, it can also be displayed in real time next to the values from previous exam image which needs to be reproduced.

Figure 30:
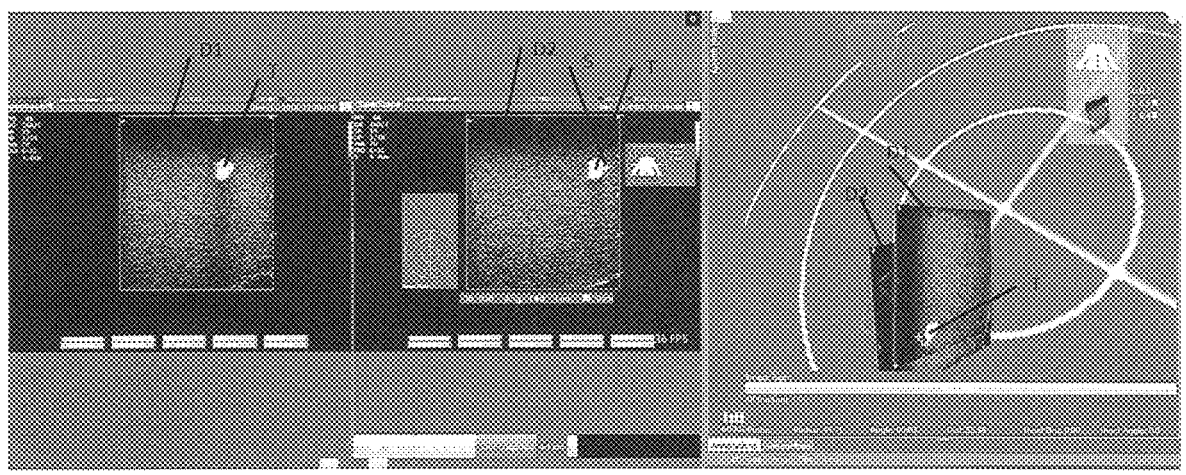
FIG. 30 is an example of a target relocation screen with multiple guides for probe frame, target and body position/orientation relocation and matched current and previous images.

When all or some of the conditions above are met (FIG. 37), the TDMD can issue a confirmation signal S of image relocation or matching between the previous and current images. The flowchart in FIG. 37 is a non-limiting example and the conditions described in FIG. 37 to achieve target relocation can be used in any combination or order. Any graphical, alphanumerical, sound or other can be used for this purpose (FIG. 30).

Figure 16:
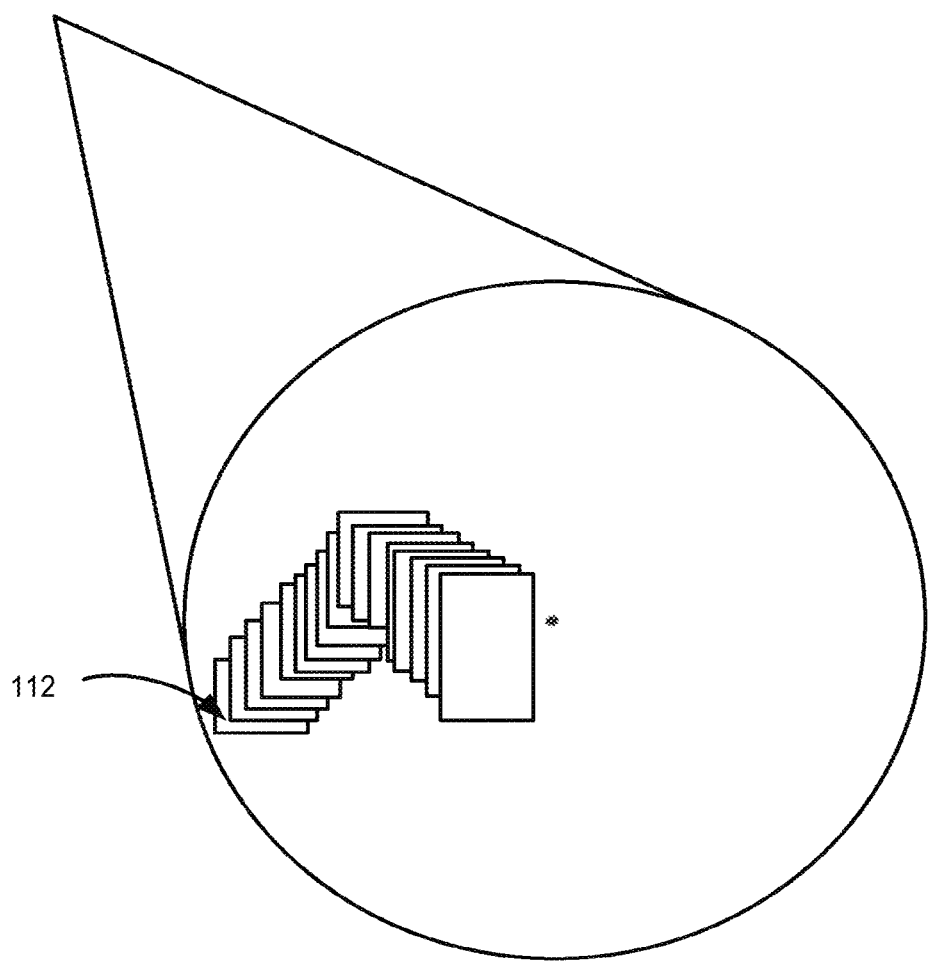
FIG. 16 depicts a display screen shot illustrating positioning of ultrasound frames in one video clip over a body diagram.
Figure 17:
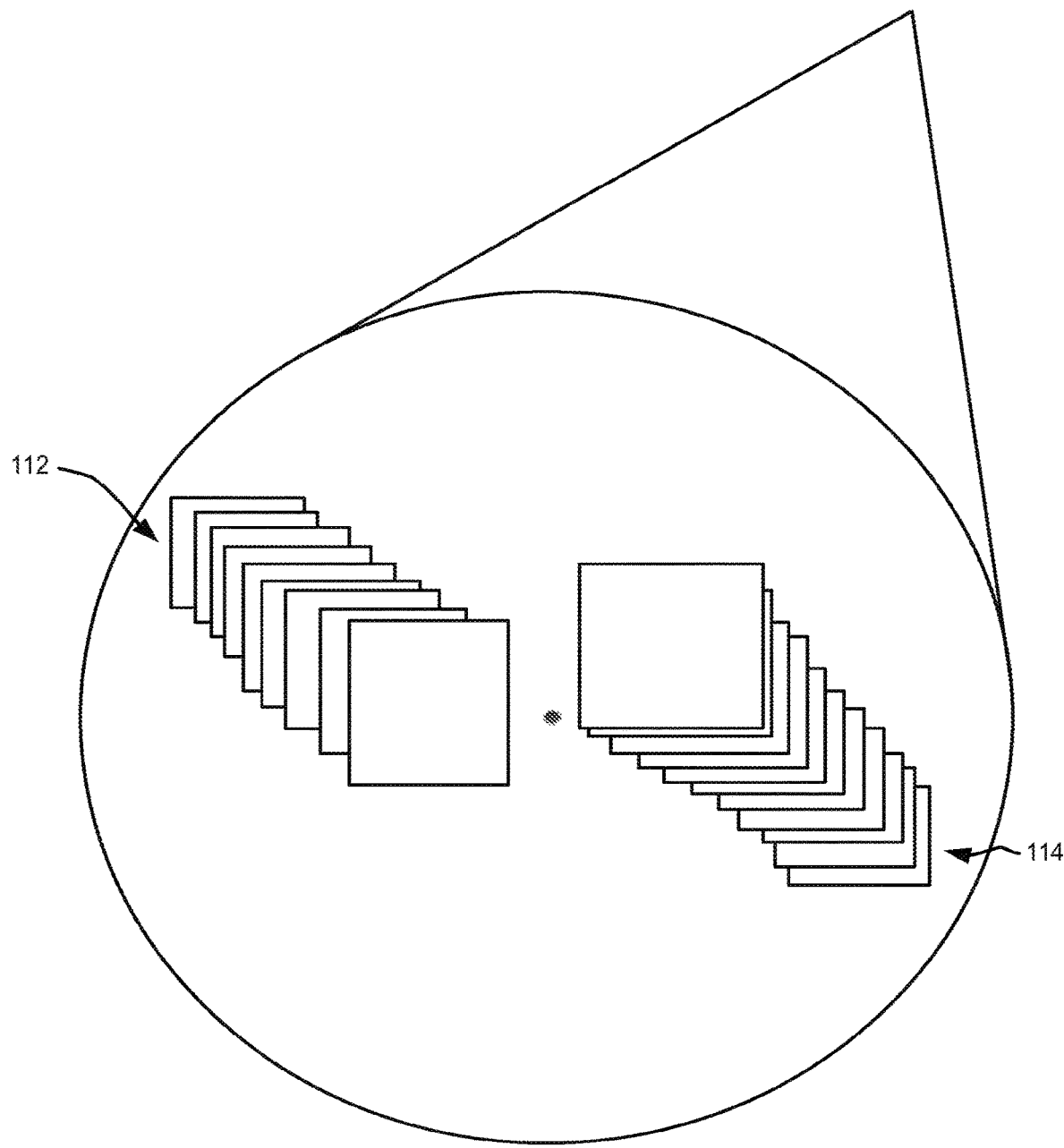
FIG. 17 depicts a display screen shot illustrating positioning of ultrasound frames in multiple video clips over a body diagram.
Figure 32:
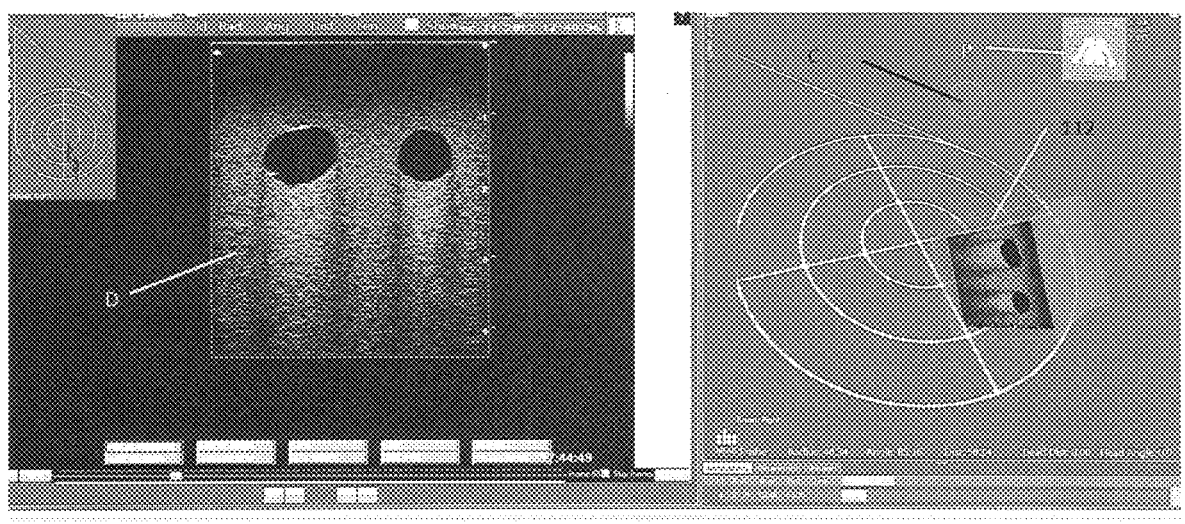
FIG. 32 is an example of an ultrasound video clip with each frame displayed over the body diagram aligned with the patient's orientation planes.

TDMD enables a user to record multiple ultrasound free hand 2D frames in a video sequence (clip) or cine loop, with each frame saved with the real time positional coordinates relative to the anatomical references as described before. When using the positional information in the multiple 2D frames of one or more video sequences corresponding to a scanned volume, the 2D images can be reconstructed in 3D volume images corresponding to the scanned region, using known 3D reconstruction algorithms. The 3D volume reconstruction can be obtained from the original captured 2D ultrasound images or the segmented or otherwise processed 2D images in a video sequence. The position of each 2D frame, used to reconstruct the volume images, is recorded relative to the real time anatomical references positions and therefore the reconstructed volume images are corrected with respect to the patient body position, orientation and tissue movements during scanning. As previously described real time ultrasound images position and orientation to the body and anatomical references like nipple C can be calculated over co-registered secondary sets of images of the same body region (diagram 101) and displayed (FIG. 31) or saved for later review. Using scanning protocols dedicated to the examined region, the 2D ultrasound images in video clips from a whole body region, part or organ can be obtained and reconstructed in 3D volume images. For example, a whole breast can be scanned in adjacent parallel, radial or circular rows, with each row recorded as a video sequence of 2D ultrasound images, with corresponding positional data referenced to the anatomical references, like nipple C, body position P, 112 in FIG. 16, FIG. 32. Also a multitude of video sequences to cover the entire breast region and the multiple 2D frames in a video clip or multiple video clips can be obtained and displayed during the image acquisition or after the acquisition 112, 114 in FIG. 17 and FIG. 33.

Figure 33:
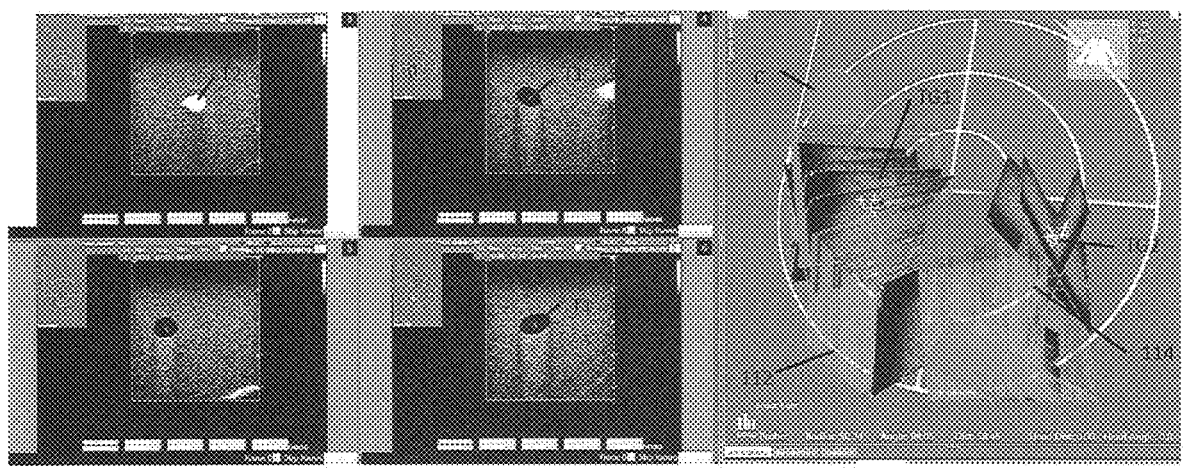
FIG. 33 is an example of multiple ultrasound video clips and individual frames, with each frame displayed over the body diagram aligned with the patient's orientation planes. Target marks and frames corresponding to same lesion are grouped together.
Figure 34:
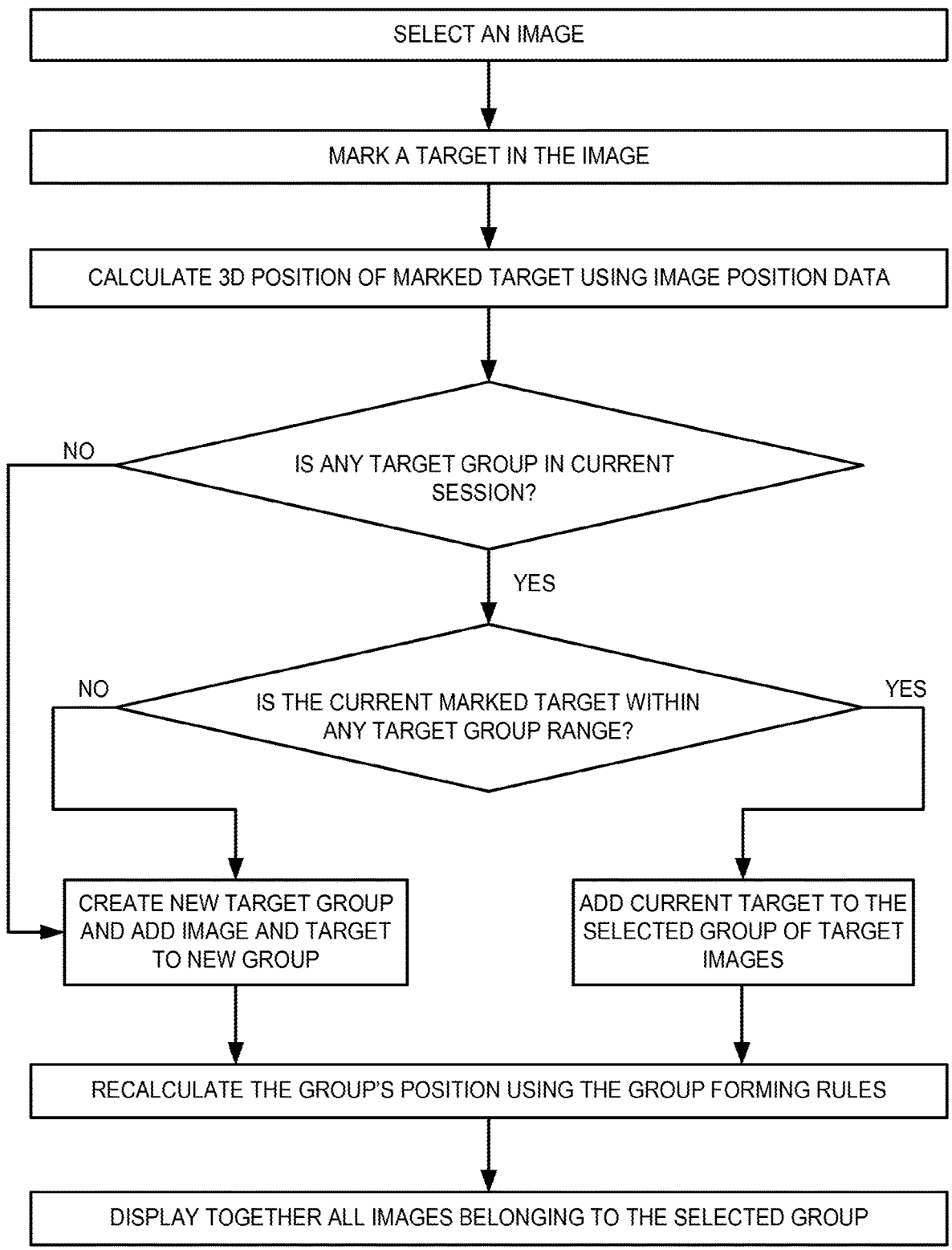
FIG. 34 shows the steps required to perform the grouping and display of images containing same target.
Figure 35:
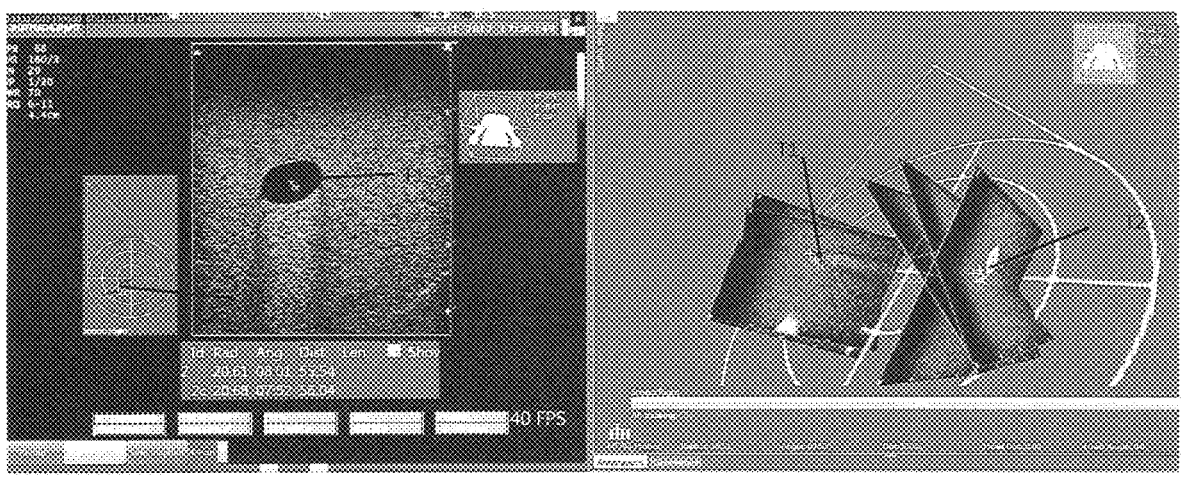
FIG. 35 is an example of a display with ultrasound images containing same target grouped together over the body diagram.

When multiple still images of the same lesion are captured and recorded with the hand held ultrasound probe from different positions and orientations, the lesion appearance can change, for example an oblong mass shown in longitudinal and transverse cross sections. It is also possible that two or more different lesions have a similar appearance in multiple ultrasound images, for example multiple cysts in the breast or other body part. The manual annotation of images with lesions described above can be difficult and prone to errors which would lead to diagnostic interpretation errors. It would be therefore desirable to accurately determine the position of each lesion or target and group together all images containing the same lesion or target to aid the image interpretation. This feature would result in reducing the number of diagnostic errors and speed up the images interpretation process. The accurate position measurement of the targets is done by the TDMD. The positional data associated with each image and target is processed (FIG. 34) and all images containing targets within a determined range can be displayed together. FIGS. 35, 33 show 2 targets, T1 and T2 with corresponding images in the target groups TG1 and TG2 over the breast diagram. The spatial range used to group images with the same lesion can be determined by manual, automatic or any other segmentation method. An additional tolerance can be allowed to include all images of interest. One non limiting method would be to measure 2 or 3 orthogonal axes of a target and generate a 2D or 3D shape which would contain the target. Subsequently, all images containing a region with the determined positional coordinates are grouped and displayed together. The display of the images can be done by showing all images in a group next to each other. At the same time or separately, images in a group or multiple groups, first set of images, can be displayed over a body diagram or other body representation, coregistered with the ultrasound images, second group of images. Image markers at selected targets, generated in the 2D or 3D displays, can be displayed over the body diagram. (FIGS. 35, 33) Using the above display method, cropped images of targets, multiple sequential frames in video clips or reconstructed 3D images can be grouped and displayed together. The group display can be performed during images acquisition by the operator or later at interpretation.

It is also possible to perform the group display method with images from different temporal exams of same region and patient, to facilitate the comparison of same target or lesion recorded at different times.

Figure 18:
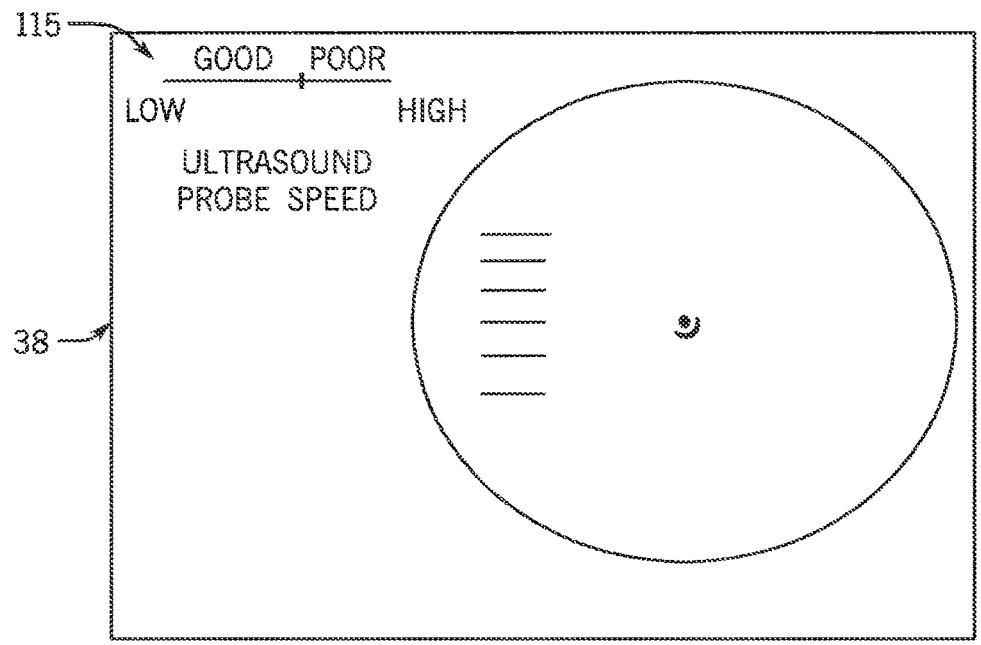
FIG. 18 depicts a display screen shot illustrating probe speed display with probe and frame positions over a body diagram.

When the free hand ultrasound is used to obtain video sequences for direct review or 3D reconstruction, the probe speed over the skin and the probe orientation are important factors for the quality of the 3D reconstructed images. A constant probe movement with the speed matched to the ultrasound frame rate and the scanning plane of each 2D frame parallel to each other, in multiple consecutive frames, is desirable for accurate 3D volume reconstruction or recording of successive 2D frames in video clips at short uniform distance between the frames to allow the detection of small targets. The real time scanning plane can be visualized during scanning, displayed over the body diagram and the operator can adjust the probe position as needed to obtain good quality 2D images. The ultrasound 2D image plane position and orientation in consecutive frames can be compared and the angles between the axes in consecutive planes calculated and displayed, with warnings set when exceeding the predetermined range for an accurate 3D reconstruction. An on screen indicator can show the real time ultrasound probe speed and guide the operator to maintain the probe speed within the recommended range for the ultrasound machine settings (FIG. 18). At the same time, the ultrasound machine frame rate could be automatically adjusted, within the available range, by the TDMD application. The probe speed can be determined from the positional sensor or sensors attached to the ultrasound probe and anatomical references. The ultrasound probe translation and rotation speeds, and its position/orientation can be continuously monitored by the TDMD computer and a quality factor associated with each frame or video clip. This feature allows for the rejection of images which are not within a specified range of values.

The cumulated display of the acquired images during and after an exam, allows the operator or interpreter to assess the total area or volume covered by the saved images (FIG. 33).

By tracking the scan head position of the ultrasound probe when in the proximity of the examined body part, a cumulative map of probe positions can be generated to assess the total area scanned by the operator (FIG. 27). This feature can be useful when a limited number of still images are recorded, as it is done with most exams performed by technologists or other operators other than the images interpreter, and later the interpreter, usually a physician, can document the scanned area over the body diagram.

Figure 20:
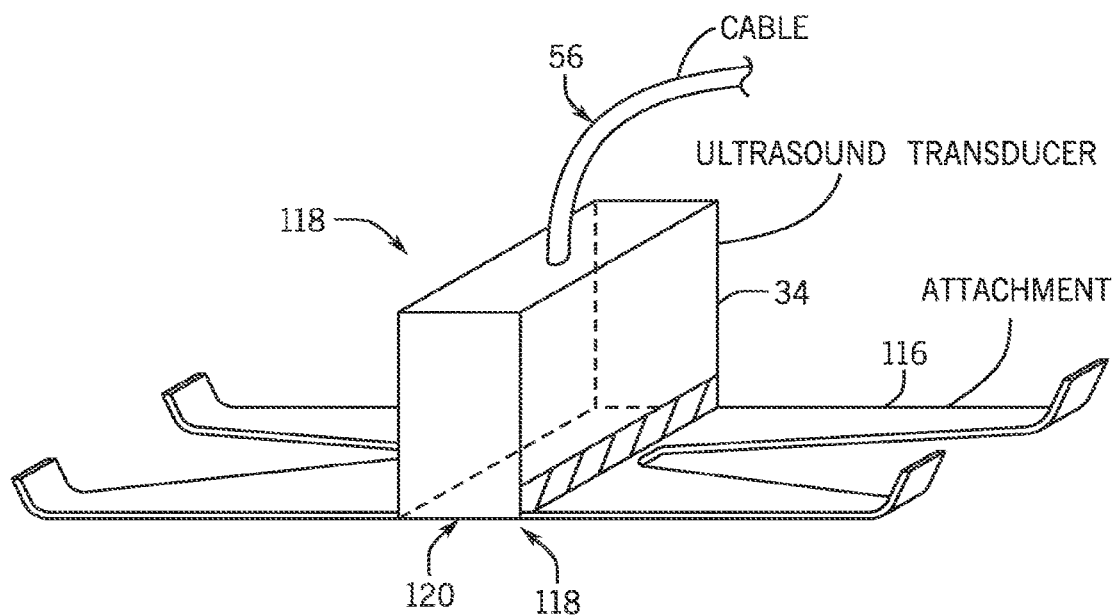
FIG. 20 depicts an ultrasound probe attachment for breast ultrasound.

During the sequential multiple ultrasound frame acquisition in a breast ultrasound exam, it is desirable to maintain the scanning plane, in multiple consecutive frames of a video clip, as parallel as possible to each other and a perpendicular angle to the breast skin, to maintain uniform spacing between the 2D video frames, for accurate 3D reconstruction and reproducible results. It would be also helpful to minimize the breast tissue deformation during scanning, which would also help obtain reproducible 2D, 3D measurements and reconstructed images from the video clips, also minimize skin fold and other artifacts. To address the above, a dedicated ultrasound probe head attachment device can be used. The device consists of an ultrasound probe holder which attaches to the ultrasound probe (FIG. 20). The described ultrasound probe attachment has a flat smooth surface with raised margins 116 attached to the ultrasound probe 34, to allow sliding over the breast skin, while holding the attached ultrasound probe scanning plane perpendicular or at an angle to the flat surface of the attached device. The flat surface is cut in the central region to allow the ultrasound probe to be positioned in close proximity to the nipple, without touching or otherwise changing the shape and position of the nipple and/or the nipple attachment device 92.

The ultrasound probe 34 position in reference to the attachment part 116 can be locked at a fixed position or it can be changeable during scanning, in 1 or more directions to allow optimal quality for the ultrasound images.

Figure 21:
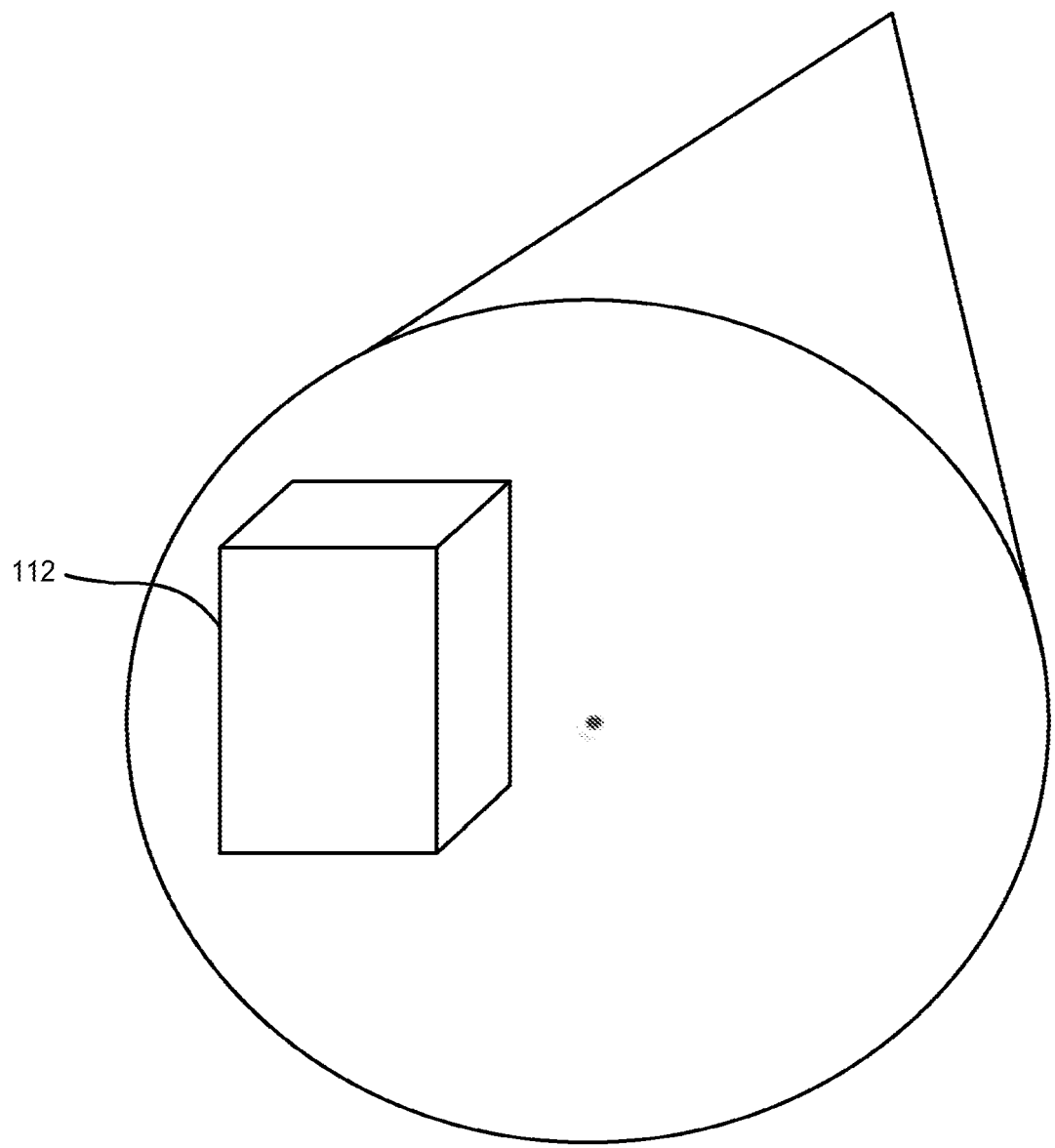
FIG. 21 depicts a display screen shot illustrating a reconstructed volume displayed over a body diagram.
Figure 22:
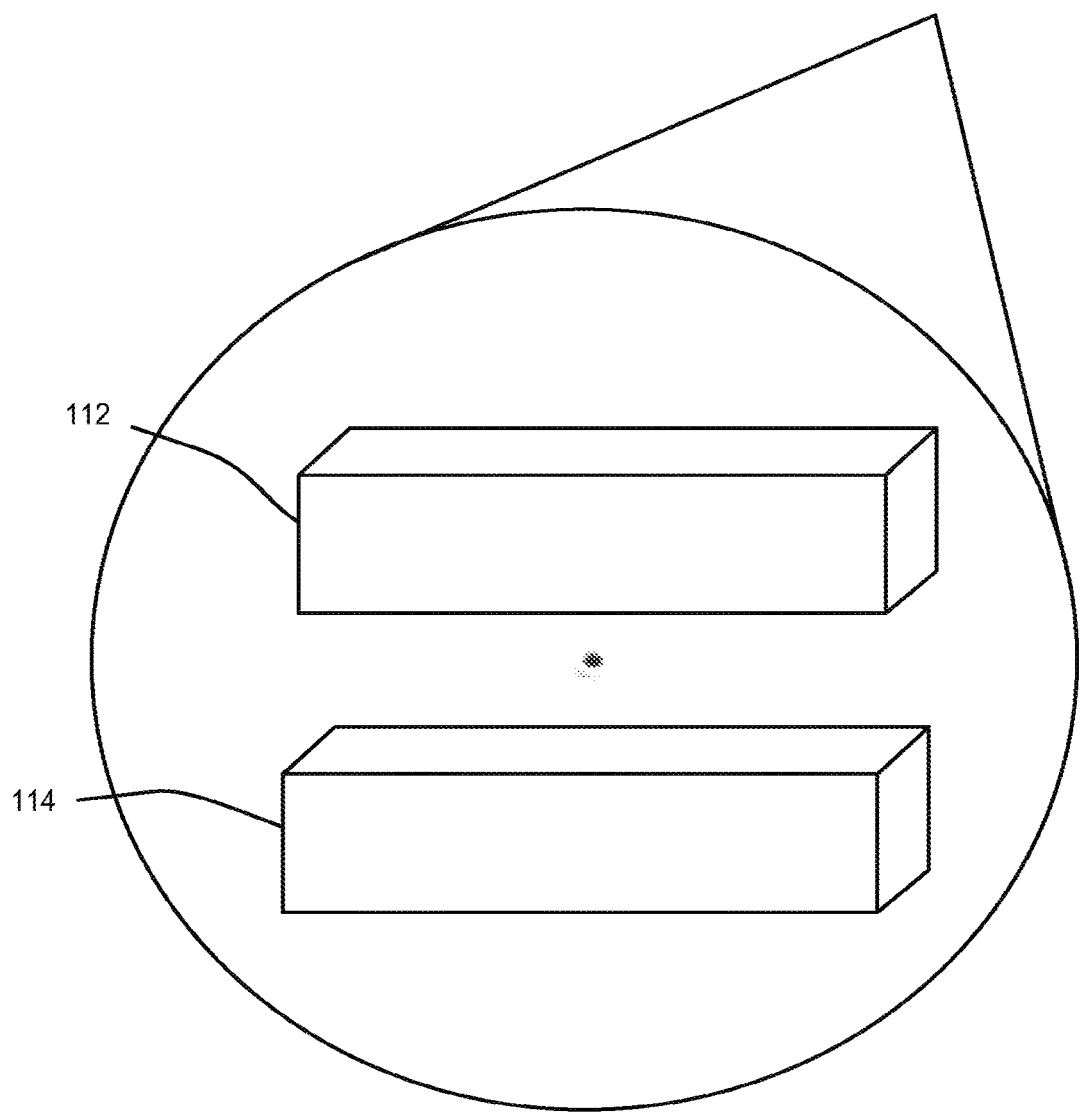
FIG. 22 depicts a display screen shot illustrating multiple reconstructed volumes displayed over a body diagram.

Each 3D set of images contains the positional information from the source 2D images, in relation to the real time anatomical reference or references position, obtained during ultrasound scanning. One or more 2D or 3D sets of images, each set obtained from a video sequence, can be displayed over the body map at the same time (FIGS. 21, 22). The 3D image sets are positioned and oriented relative to the selected anatomical reference(s) including the body position relative to the exam table, to create a larger volume comprising the entire region of interest, as it can be done with 2D single or multiple ultrasound images, as described above. The separate individual 3D image volume sets can be realigned, coregistered manually or automatically, if needed, using more internal and external positional references, to create an entire cumulated volume from multiple 3D volume sets which more closely resembles the whole real target volume. Additional positional references may be represented by same structures detectable in multiple images or image sets, sensors or markers with known positional coordinates and the coregistration of multiple images can be performed using known coregistration algorithms.

The 3D positions of individual ultrasound frames, multiple ultrasound frames or corresponding reconstructed volume or volumes obtained with the dynamic referencing method described with the patent application, can be registered with and represented over a body map or body part map, including realistic maps obtained from the patient's measurements, real patient photographic data or other imaging modality data like CT, Mammograms, MM, PET, SPECT, etc. (FIG. 92, diagram 102).

The above positional information obtained with the dynamic referencing method described with the invention and associated with the ultrasound images, can be used to display the original or processed 2D or 3D ultrasound images over a real time coregistered body diagram, map or other 2D or 3D set or sets of body images. The associated ultrasound probe position and orientation can be displayed at the same time with the other images. The displaying of the ultrasound images over other coregistered body diagrams or other images can be performed in real time, to guide the ultrasound operator during scanning, or at a later time on a local or remotely located image viewer.

Figure 40:
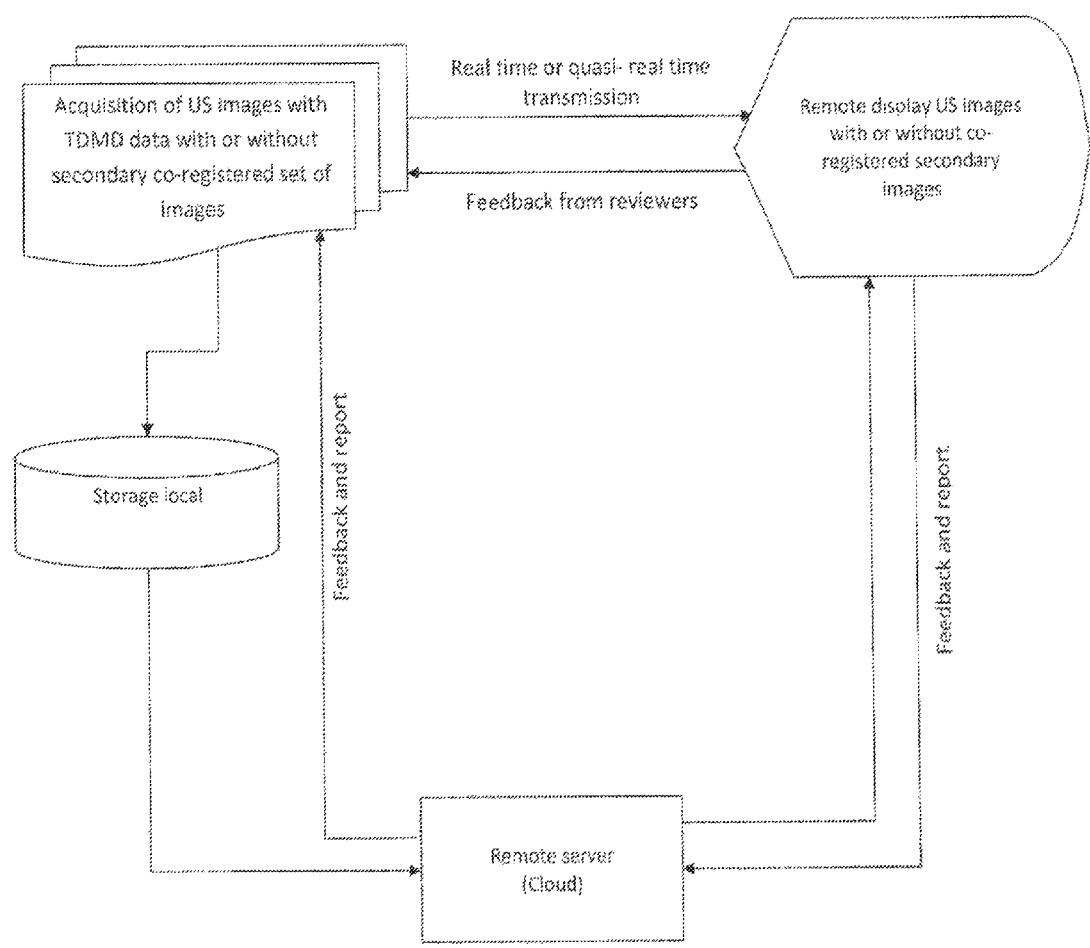
FIG. 40 with an example for remote interpretation of images acquired with the TDMD.

The real time or near real time display of ultrasound images, described above, can be performed at the local computer or at a remote viewing station or stations, where the images from the local computer are immediately transferred to the remote interpretation stations over a network system, internet connection or any other connectivity system. The remote viewer can review the transferred images in near real time or at a later time and provide feedback to the ultrasound operator regarding the ultrasound exam in progress or after its completion. The remotely transferred ultrasound images can be stored at remote or local locations (FIG. 40).

Figure 39:
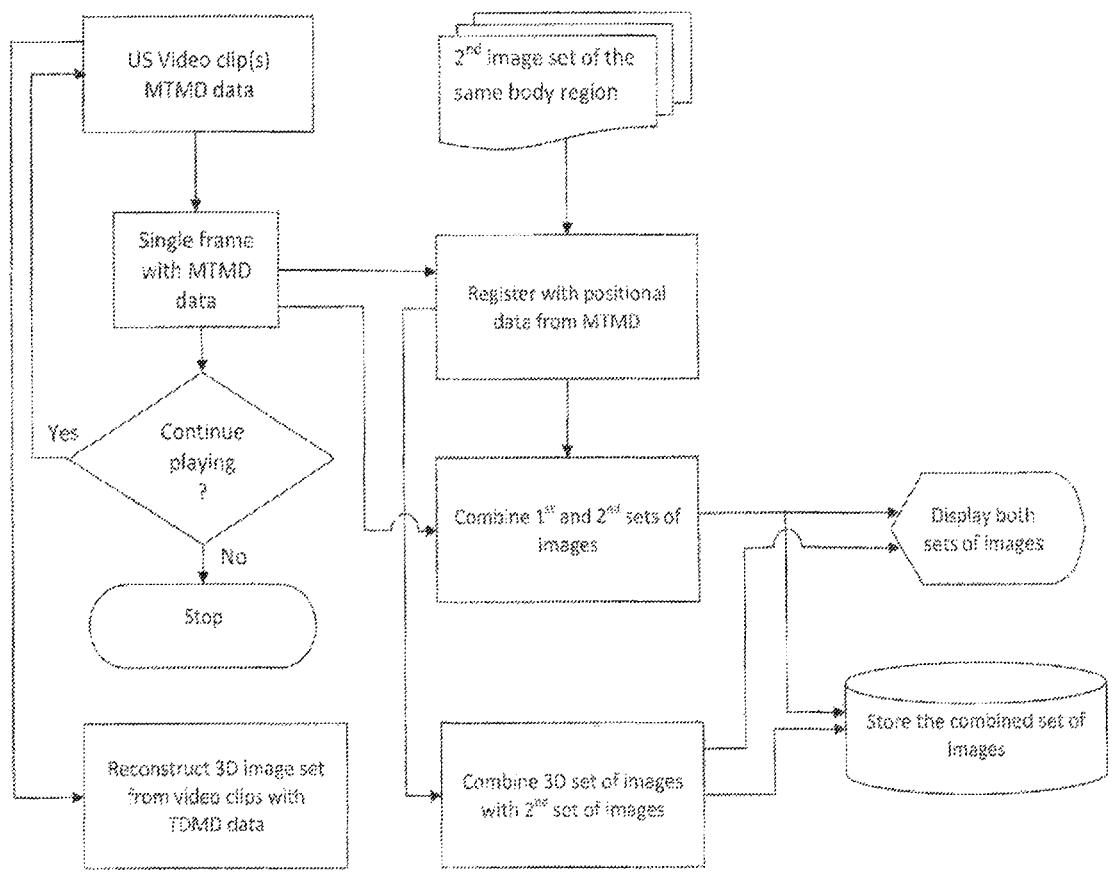
FIG. 39 shows the steps required to coregister recorded ultrasound images with a second set of images of same body region.

The original or processed 2D or 3D ultrasound images with associated positional information obtained with the dynamic referencing method described with the invention, with or without other corresponding coregistered body maps or images, can be stored in a computer memory or other data storage media. The stored images with corresponding positional information can be transferred to remote locations for viewing and interpretation. The coregistration of the ultrasound images with other body maps or images can be performed during scanning the patient or at a later time, at a local or remote computer (FIGS. 39 and 40).

Figure 23:
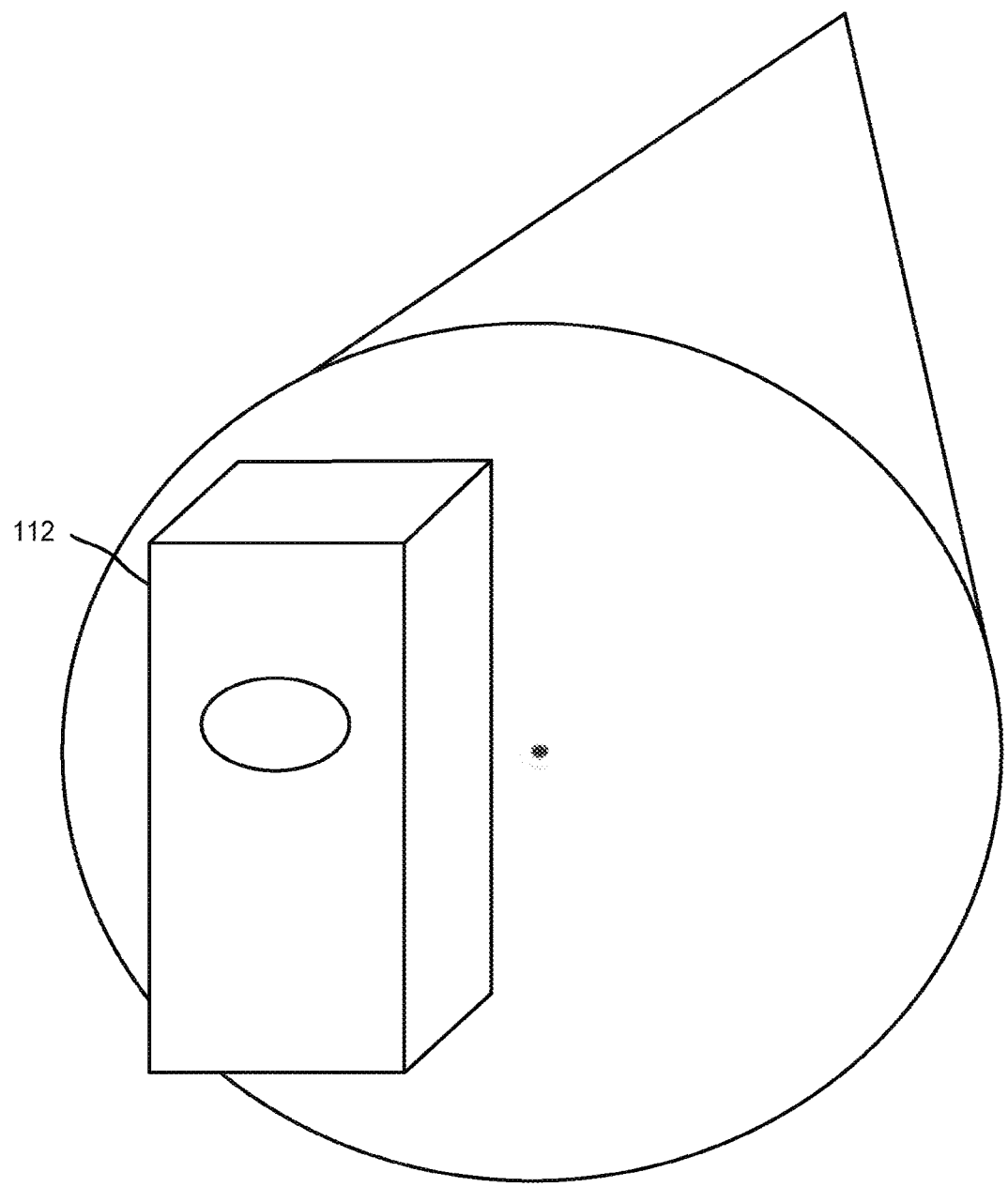
FIG. 23 depicts a display screen shot illustrating a reconstructed volume of a video clip with the reconstructed volume of an internal lesion, displayed over a body diagram.

Three dimensional images of smaller target volume structures, like tumors, cysts or ducts positioned in the larger volume images obtained from the free hand 2D ultrasound images, can be extracted using known segmentation algorithms and the obtained target volume can be displayed over 2D or 3D body maps with the position and orientation recorded during the image acquisition (FIG. 23).

The obtained sequences of 2D images in the video clips and the reconstructed 3D volumes can be displayed in a viewer for interpretation. The viewer allows for the playback of the 2D ultrasound images captured from the ultrasound machine at the acquisition speed or different speeds including frame by frame navigation. When an abnormal finding is detected, the corresponding 3D reconstructed images can be aligned in any plane with the 2D image for direct comparison, when using the positional data associated to each image pixel or voxel, obtained with the described dynamic referencing method to match the pixels or voxels positions in the different images data sets, as described above with the group display methods. The reconstructed 3D images from different video clips covering the same region of interest detected in the 2D images can be displayed at the same time with the 2D images in multiple windows and aligned to the point of interest to facilitate the diagnostic process (FIG. 33).

One or more 2D frames or a 3D image with known spatial coordinates, captured from the ultrasound machine in real time during an ultrasound exam or during later image review, can be simultaneously displayed with one or more of the corresponding 2D or 3D images with the same spatial coordinates to the anatomical reference or references, obtained during the same exam session or at a previous exam. The positional data associated to each image pixel or voxel, obtained with the described dynamic referencing method is used to match the pixels or voxels positions in the different images data sets and group multiple sets of images as described above. (FIG. 33). A sectional image from a 3D reconstructed set can be simultaneously displayed with a sectional image with the same spatial coordinates obtained from a different video sequence of the same body region and the 2D ultrasound frame with the closest matching positional coordinates to the displayed sectional image when using the positional data associated to each image pixel or voxel, obtained with the described dynamic referencing method to match the pixels or voxels positions in the different images data sets. The above displaying method which is applied to single frames or sectional volume cuts can be applied to consecutive frames or sectional volume cuts in a video sequence of frames or by scrolling through a reconstructed volume set.

When single frames are recorded for further evaluation and interpretation, each single frame can be automatically associated with a short video clip containing the frames immediately preceding the still frame acquisition, by creating a buffer with the video frames during scanning. This feature would allow the display of multiple frames or reconstructed 3D images for each still image, using the described display methods, to aid the diagnosis and interpretation.

The obtained 2D and 3D images can be analyzed together which could help the detection of shadow artifacts, increase the detection rate of small targets etc. Further processing of the obtained images using computed assisted diagnostic (CAD) software, subtraction algorithms and other processing methods can be used to enhance the diagnostic value.

The above embodiment may be used for ultrasound breast cancer screening or diagnostic breast ultrasound exams, however the same method can be applied to other regions in the body like, but not restricted to the eye, liver, abdomen, neck, kidneys, etc.

The accurate 3D reconstruction of the eye and other orbital structures can provide important diagnostic information for lesions at the orbit and the other parts of the body. For example, multiple studies demonstrate increased values of the intra cerebral pressure (ICP) are associated with the enlargement of the optic nerve sheath (ONS) behind the eye. Increased ICP can be associated with traumatic brain injury (TBI), stroke, brain tumors and other intra cerebral pathology. The early detection of increased ICP is essential for the patient's treatment and management which can save lives and prevent long term disability. The size of the ONS is in the range of few millimeters (mm), with the normal diameter of less than 5 mm. The measurements in the 2D ultrasound images are operator dependent and limited to the scanning plane, it is therefore desirable to obtain accurate 3D images of the ONS to increase the accuracy and precision of the measurements and detect small changes in the size of the ONS, to better correlate with the ICP changes. The accurate 3D reconstruction of the ONS and other orbital structures can be degraded by the head or skull motion and the intra orbital motion of the eye and attached structures during the ultrasound images acquisition. It is therefore desirable to account for both types of motion, for the 3D reconstruction of the orbital ultrasound images.

Figure 41:
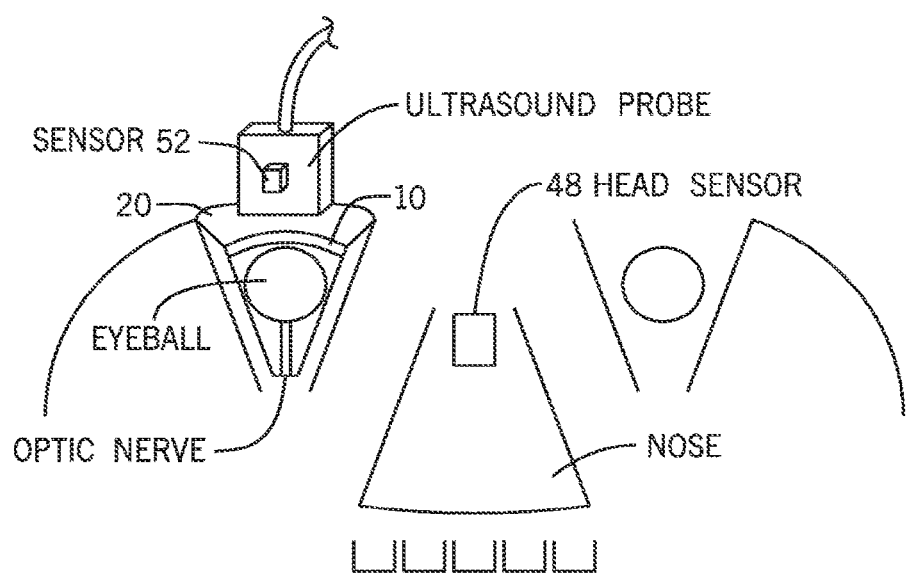
FIG. 41 shows an ultrasound transducer during eye scanning with the TDMD.

The eye and orbit ultrasound can be performed with the closed eyes, through the eye lid. A stand-off ultrasound transparent pad 10 can be applied over the closed eye lid 20 and used to facilitate the scanning and improve image quality (FIG. 41).

Figure 42:
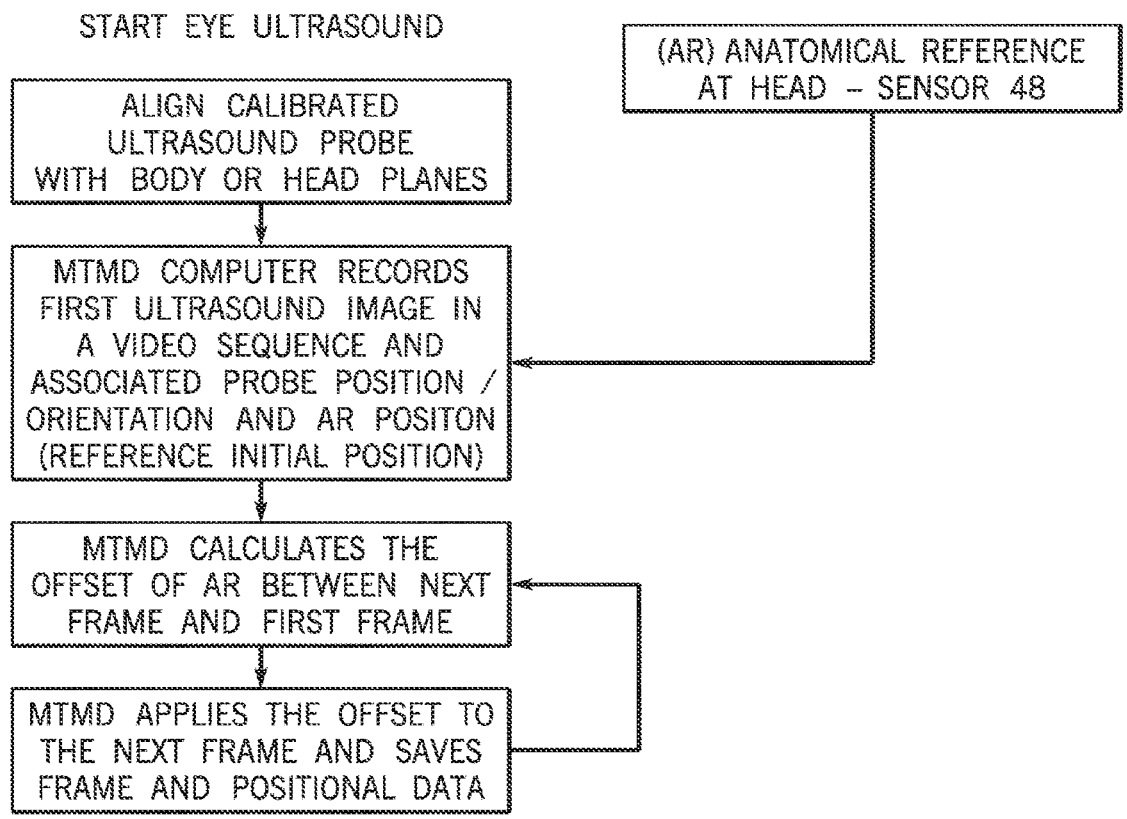
FIG. 42 shows the steps to acquire images and reconstruct volumes of orbital structures.

In the embodiments where TDMD is used and the multiple sequential 2D images in the video clip or video clips are obtained while scanning the eye and orbit structures, the anatomical reference sensor or sensors can be firmly attached to the head structures during the image acquisition process. The continuous measurement of positional data from the anatomical reference sensor or marker is used to adjust the positional data in each 2D ultrasound image in the video clips and compensate for the head motion during the scanning process (FIG. 42). For example, the attachment of the reference sensor at the upper incisor teeth can be used, since the attachment of the upper teeth to the bony skull is firm enough to allow the accurate measurement of the bony orbit real time motion.

In addition to the skull motion during the eye and orbit ultrasound exam, the eye motion in the orbit can be present and interfere with the accuracy of the positional mapping of the orbit structures relative to the anatomical reference sensor or sensors. One method to reduce the involuntary eye motion in the orbit is to instruct the conscious patient to keep the eyes open and continuously look without blinking at a fixed point, during the image acquisition. The ultrasound operator can gently pull the eyelid with the fingers and cover the eye to be examined, before applying the gel and starting the ultrasound examination of the orbit. The other eye continues to be kept open without motion. The intra orbital motion of the eye can be measured in each ultrasound individual video clip and in multiple video clips obtained during the same examination with the skull anatomical reference positional sensor or sensors kept at the same location. The position of one or more orbital references can be measured and evaluate the intra orbital motion of the orbit structures. For example the position measurement of a point or points at the center of the optic nerve attachment region to the posterior eye can show the extent of optical axis or eye globe motion among multiple video clips of the orbit obtained during the same exam. The detected motion measurements can be applied to realign the positional data in each 2D ultrasound frame of the corresponding video clip or the reconstructed 3D images, to match the positional data of one or more separate video clips obtained in the same examination. The image sets with the realigned positional data can be used for the 3D reconstruction of the region of interest from multiple video clips or 3D data sets of the same region of interest. For the images where the intra orbital motion is measured and exceeds a predetermined threshold, the corresponding images can be excluded from the 3D reconstruction of the target region to prevent the reconstruction accuracy degradation FIG. 43. The separate measurement of the head and intra orbital eye motion can be used to correct for motion artifacts.

The intraorbital eye ball motion relative to the bony orbit can be measured at the scanned eye or the contralateral eye, since the eye motion is conjugated.

The intra orbital motion of the orbit structures can be measured with an active real time motion sensor or sensors applied at the eye. For example a small magnetic sensor could be attached at the anterior sclera during the ultrasound exam. In a different embodiment a passive marker, which can be identified in the ultrasound images, can be applied at the anterior sclera and its position in the ultrasound images may be used to measure the intra orbital motion of the eye, optic nerve and other orbital structures. The positional change of the marker or position sensor, relative to the anatomical sensor applied at the skull, measures the degree of intra orbital motion of the eye and other orbital structures). The position marker can be echogenic with a curved linear shape, single or multiple echogenic points, or any other size, shape and appearance which can be identified in the ultrasound images.

The dynamic position measurement of the head's anatomical reference or any other anatomical reference during the ultrasound exam, obtained with continuous position measurements from the attached sensors or markers, can be replaced with "snap shot" measurements of the anatomical reference position. For example, it can be obtained by applying the center of the calibrated ultrasound probe with the positional sensor at the anatomical reference and record the anatomical reference position corresponding to the center of the ultrasound probe. The individual "snapshot" measurements of the anatomical reference position can be repeated during the ultrasound exam, for example between multiple ultrasound video clips acquisition or between individual ultrasound frame acquisition. The advantage of the individual "snapshot" measurements of the anatomical reference position is that it does not require a positional sensor or sensors attached at the anatomical reference; however it has the disadvantage of not being able to dynamically record the anatomical reference position during the ultrasound images acquisition.

Figure 43:
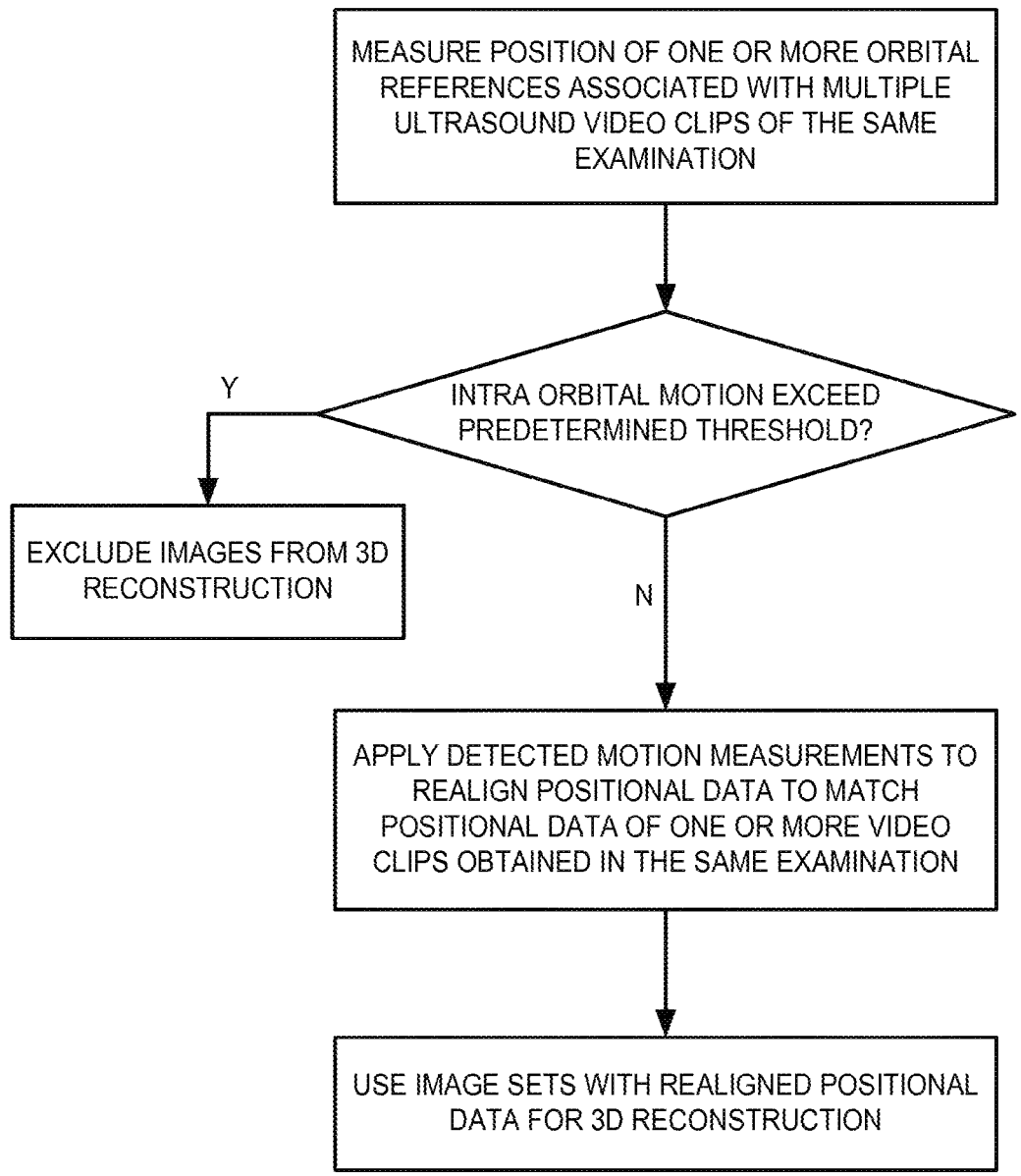
FIG. 43 shows the steps to correct motion artifacts in 3D images using detected intra orbital motion.

To further improve the dataset selection for the accurate 3D image reconstruction of eye or orbital structures, it is important to select the ultrasound images where the eye ball maintained the same position in reference to the orbit. This task can be performed by using an eye tracking device or method as described above or different, to the contralateral eye and match the ultrasound images where the eye ball tracking device confirmed the position of the eyes in the orbit within a range where the reconstruction of 3D images is of acceptable accuracy for diagnostic or treatment purposes (FIG. 43).

For diagnostic and treatment purposes, it is important to associate the diagnostic images with the clinical findings obtained by palpation, visual inspection or any other method. For example, the breast palpation is a frequently used method for the breast evaluation. The correlation with the diagnostic imaging information can be difficult or impossible, especially for the small tumors or other palpable masses. It is therefore desirable to correlate the position of the examiner's finger pointing at the clinical abnormality with the diagnostic images obtained in the same region of the breast.

Figure 24:
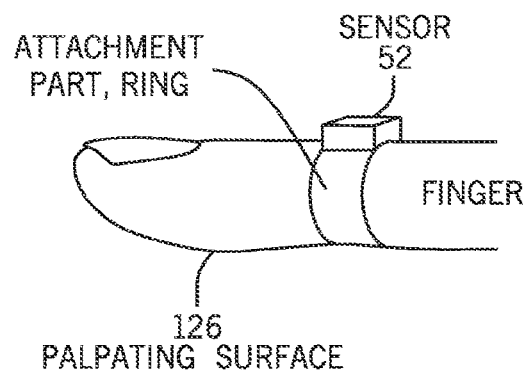
FIG. 24 illustrates a side view of a finger with sensor 52 for palpation correlation with ultrasound images.
Figure 25:
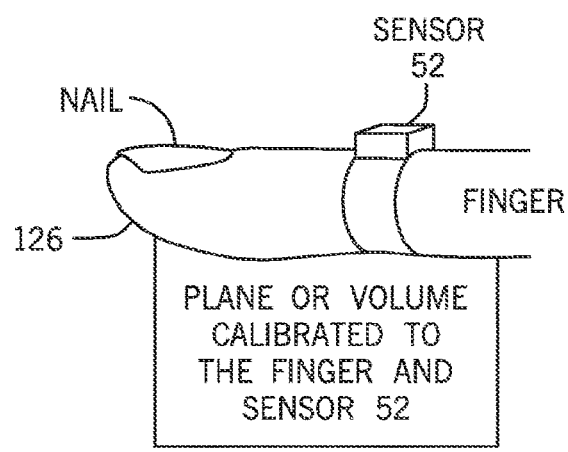
FIG. 25 illustrates a side view of a finger with sensor 52 and calibrated plane for palpation correlation with ultrasound images with ultrasound display frame.

In an embodiment of the above invention, one or more positional sensors or markers can be applied at the examining finger or fingers (FIG. 24). The position sensor or marker can be attached at the finger remotely from the fingertip and palpating finger surface 128, to allow the unobstructed palpation of the skin. The position of the fingertip can be calibrated to the positional sensor attached at the finger in a similar way to the ultrasound probe or other object calibration process, by using one or more position transformations. For example, with the position sensor or marker attached at the finger, an imaginary plane or rectangle can be calibrated in the longitudinal plane of the phalanx, perpendicular to the nail plane, with one side parallel to the long axis of the corresponding distal phalanx and the other side perpendicular to the distal phalanx long axis and to the coronal plane through the phalanx (FIG. 25). Alternatively a volume can be calibrated to the finger. A sensor attachment part, like a ring can be calibrated to the sensor and finger. The calibrated frame can correspond to the scanning plane calibrated for the ultrasound probe used to obtain the ultrasound images in a previous exam. The positional data corresponding to the calibrated rectangle at the finger is obtained with the anatomical reference sensor(s) or marker(s) at the same body location as with the previous ultrasound exam to be matched and with the patient body position to match the body position during a previous ultrasound exam.

Figure 26:
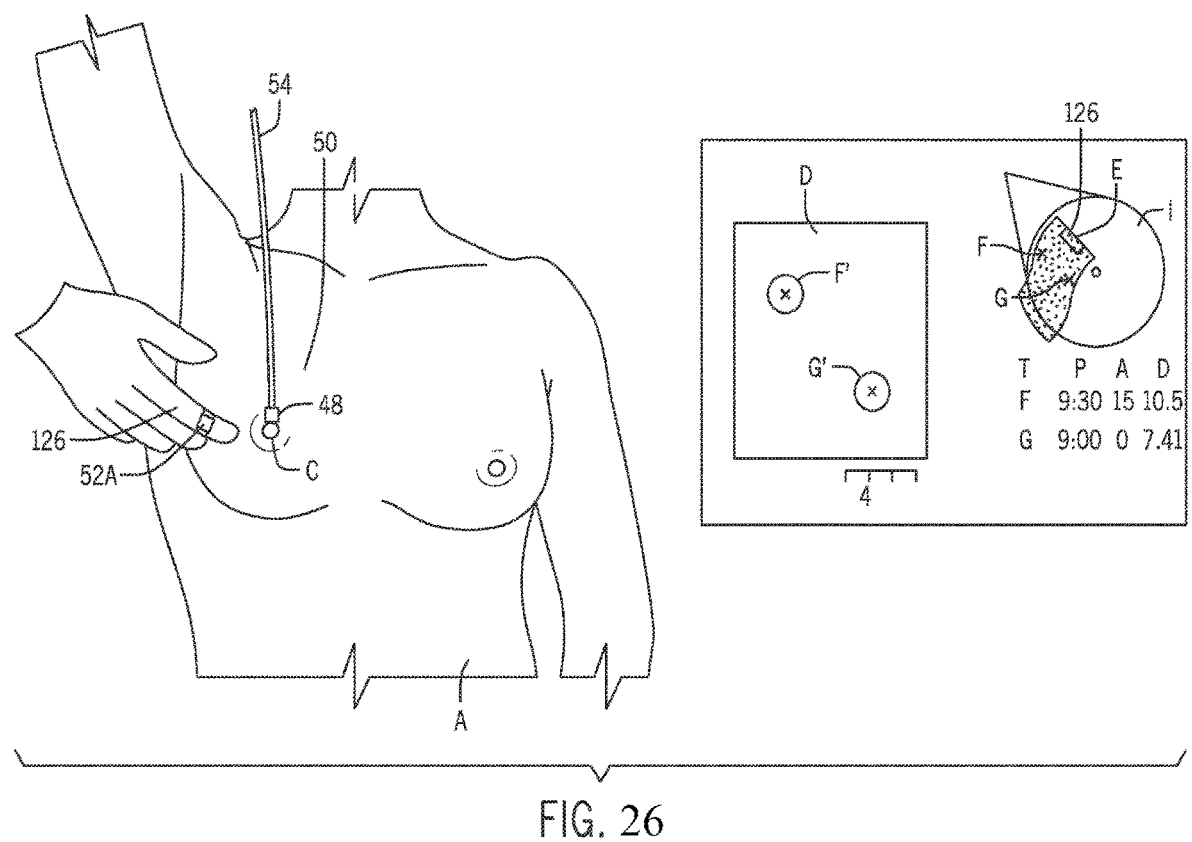
FIG. 26 describes a breast ultrasound exam with palpation correlated with the display of ultrasound images from a previous exam.
Figure 36:
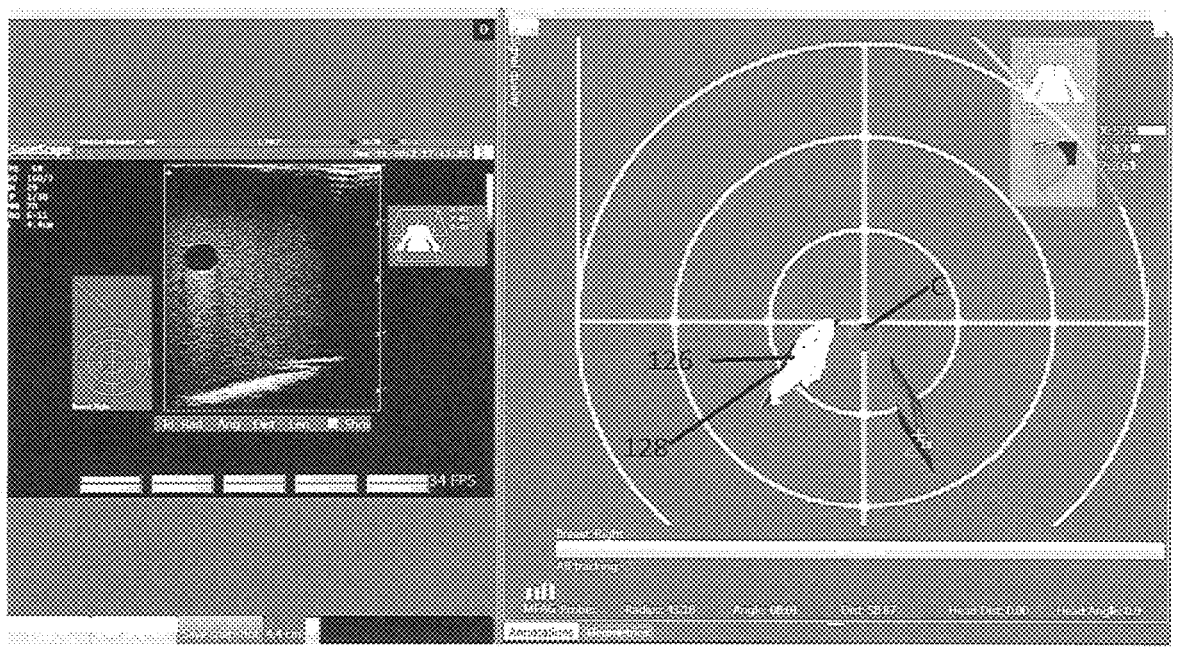
FIG. 36 is an example of a display showing the palpating finger and ultrasound images over the same body diagram.

While performing the palpation exam, the positional information from the imaginary rectangle/frame 126 calibrated at the finger can be continuously calculated and displayed over the body diagram, together with all or some of the ultrasound images from previous exams with corresponding patient's body position and referenced to same anatomical reference like nipple C. (FIG. 44, FIG. 36) Also, the 2D or 3D images with positional information, within the preset range from the palpating finger or all images are displayed in real time during the palpation examination and the examiner can instantly visualize and correlate the tactile perception at the calibrated finger or fingers with the previously acquired ultrasound images (FIG. 26).

In a different embodiment the positional sensor or sensors, can be applied at a hand held body resembling the ultrasound probe or any other object including surgical instruments and the object calibration can be performed for any point and plane, in a similar way with the ultrasound probe or the finger calibration described above. The corresponding ultrasound images are displayed while moving the calibrated object in the proximity of the previously scanned images.

Figure 44:
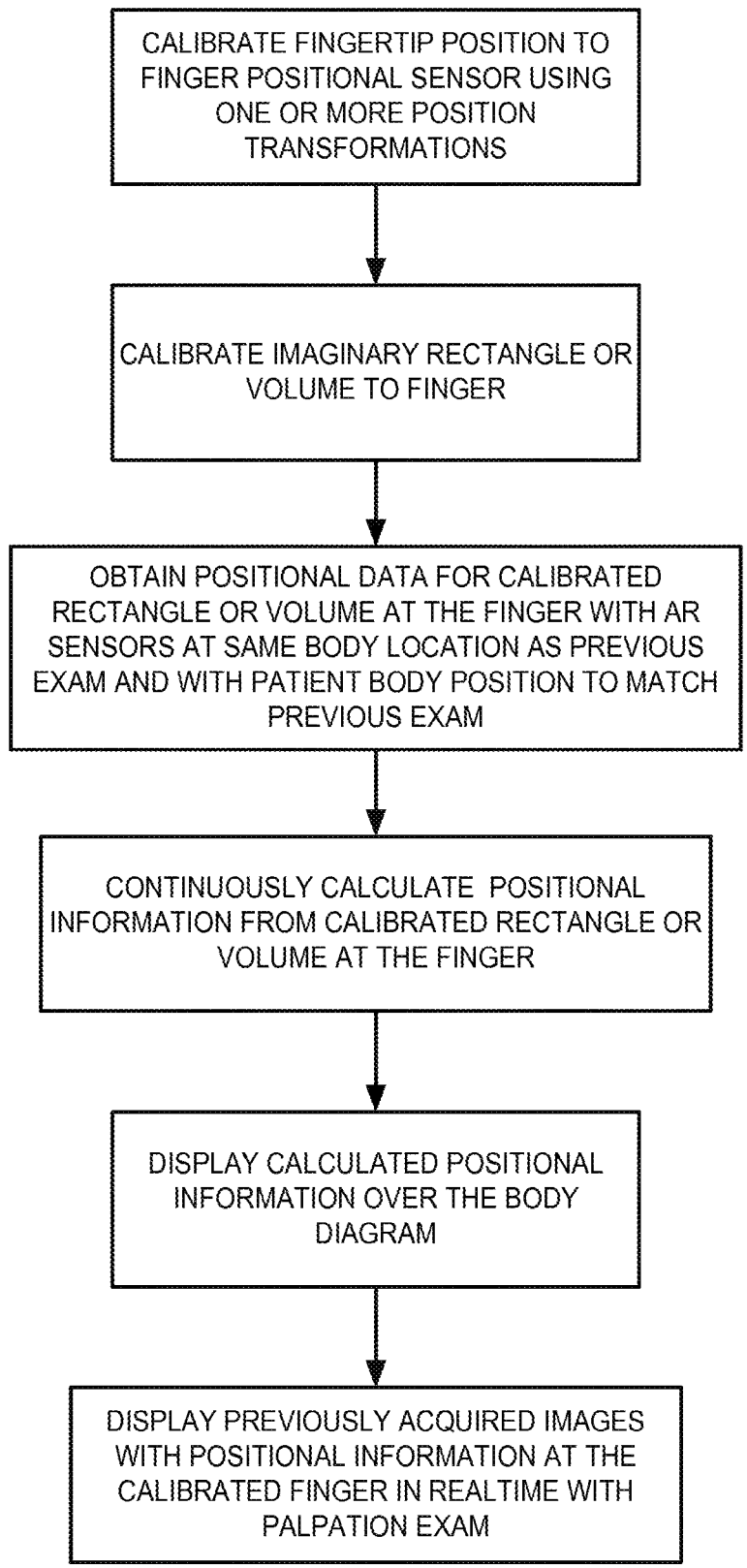
FIG. 44 shows the steps to calculate and display the position of a tracked finger over the body diagram and save positions associated with palpable findings.

The relocation method described before for the hand held ultrasound probe with the display of targets, previous exam probe position/orientation and current calibrated object or finger position over a coregistered body map or other representation can be used (FIG. 44).

The above displaying method is not limited to the ultrasound images, any images obtained with a different modality or combination of modalities, like CT, MRI, separate or coregistered in space with positional registration to the same anatomical sensor(s) or marker(s), can be displayed in a similar way, using the calibrated fingers or objects.

The images from an image producing hand held device different from an ultrasound probe, like hand held gamma cameras, near infrared hand held probes or others, can be positionally calibrated to the probe in a similar way to the ultrasound probe image calibration. The hand held imaging devices described above can be positionally tracked in real time in reference to the anatomical sensors using the same method described with the invention and the associated images positional information determined in real time and displayed in correlation with the ultrasound images obtained with the invention's tracking method or over other body maps or images after position registration.

Figure 45:
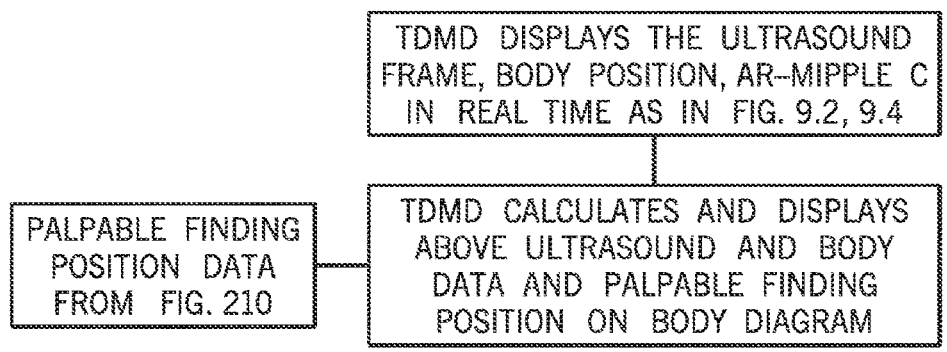
FIG. 45 shows the steps to calculate and display a palpating finger and previously obtained ultrasound images over a body diagram.

Also, in a different embodiment, the calibrated object, finger or other examiner tool can be used to obtain the positional coordinates of a target in the body, in relation to the anatomical reference sensors, in a similar way as described above. The position of a palpable finding can be calculated, displayed and saved. Subsequently, the obtained ultrasound images with the positional information in reference to the same anatomical landmarks, can be matched to the previously recorded coordinates for a clinically found lesion and help correlate the clinical findings with the diagnostic images. The same navigation method used to relocate a ultrasound image can be used to relocate a the position of a palpable finding with the ultrasound probe, calibrated finger or other calibrated object fitted with positional sensor(s) or marker(s) (FIG. 45). The method is not limited to the ultrasound images and other modality or combination of modalities images, with the corresponding positional registration and information, can be used for correlation with the clinical positional data.

The preceding merely illustrates the principles of the invention. It will be appreciated that those skilled in the art will be able to devise various arrangements which, although not explicitly described or shown herein, embody the principles of the invention and are included within its spirit and scope. For example, the described mapping, displaying and navigation, can be used to build an automated breast ultrasound scanning system. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A medical ultrasound system for enabling remote examination of a patient at an examination location, the medical ultrasound system comprising:
   a first sensor fixed to a probe head of an ultrasound probe for generating data identifying a probe head position;
   an anatomical reference sensor for tracking a position of at least one pre-selected anatomical reference on a deformable structure of the patient;
   a body sensor for dynamically tracking a body orientation of the patient in reference to a known object during an imaging session and independent from the tracked position of the at least one pre-selected anatomical reference, the body sensor registerable with at least one of body axes and planes of the patient; and
   a processor configured to:
      process data received from the first sensor, the anatomical reference sensor, the body sensor, and ultrasound frame image data during the imaging session;
      dynamically reference the probe head position and the ultrasound frame image data to the position of the at least one pre-selected anatomical reference and the body orientation of the patient based on the received data;
      load a previously obtained image of the patient, the previously obtained image comprising a marked target associated with a target of the patient;
      transmit a real time probe frame position and orientation and a second probe frame position and orientation from the previously obtained image over a same body part diagram to a remote viewing location that is different from the examination location.

2. The system of claim 1, wherein the real time probe frame position and orientation and the second probe frame position and orientation from the previously obtained image are displayed at the remote viewing location in real time.

3. The system of claim 1, wherein the real time probe frame position and orientation and the second probe frame position and orientation from the previously obtained image are stored for later display.

4. The system of claim 1, further comprising transmitting feedback from the remote viewing location to the examination location based on the real time probe frame position and orientation and the second probe frame position and orientation from the previous examination.

5. A method for enabling remote examination of a patient at an examination location, the method comprising the steps of:
   using an anatomical reference sensor to track a position of at least one pre-selected anatomical reference point on a deformable structure of the patient during a current ultrasound procedure;
   using a probe sensor to track a position and orientation of a current ultrasound probe in a body coordinate system and with respect to the at least one pre-selected anatomical reference point during the current ultrasound procedure;
   using a body sensor to track a body orientation of the patient during the current ultrasound procedure independent from the tracked position of the at least one pre-selected anatomical reference;

transmitting data acquired from the anatomical reference sensor, the probe sensor, and body sensor to a processor;

processing the acquired data to determine anatomical reference position coordinates, ultrasound probe position and orientation, and body orientation of the patient relative to a spatial reference frame generated from data transmitted from the anatomical reference sensor and body sensor;

determining a positional relation between the body orientation of the patient and a position of a reference object;

registering the position of the reference object with the spatial reference frame;

calculating position coordinates in the spatial reference frame of a target in an ultrasound image frame; and transmitting the ultrasound image frame with its associated position coordinates to a remote viewing location.

6. The method of claim 5 wherein the ultrasound image frame and its associated position coordinates is displayed at the remote viewing location in real-time.

7. The method of claim 5 wherein the ultrasound image frame and its associated position coordinates is stored for later display at the remote viewing location.

8. The method of claim 5 wherein the processor is located at the remote viewing location.

9. The method of claim 5 further comprising transmitting feedback from the remote viewing location to the examination location.

10. The method of claim 5 further comprising:

retrieving, at the remote viewing location, a stored ultrasound image frame with associated positional data acquired from the anatomical reference sensor, associated orientation data acquired from the body sensor, and associated positional and orientation data acquired from the probe sensor during a previously performed ultrasound procedure;

dynamically coregistering the stored ultrasound image from with the ultrasound image frame acquired during the current examination using the data acquired from the anatomical reference sensor, the body sensor, and the probe sensor during the current ultrasound procedure and the previously performed ultrasound procedure; and simultaneously displaying, at the remote viewing location, the stored ultrasound image frame obtained from the previously performed ultrasound procedure and the ultrasound image frame acquired during the current examination over a body diagram.

11. The method of claim 5 further comprising:

displaying, at the remote viewing location, positional coordinates of a previously recorded target located within a stored ultrasound image frame; and overlaying a current position and orientation of the ultrasound probe on the display of the previously recorded target during the current examination to guide a user to the target.

12. The method of claim 5 further comprising displaying the ultrasound image frame, the position of the at least one pre-selected anatomical reference point, the position and orientation of the ultrasound probe, and the body orientation of the patient on a display at the remote viewing location.

* * * * *